United States Patent [19]
Craik et al.

[11] Patent Number: 6,033,894
[45] Date of Patent: Mar. 7, 2000

[54] KAPOSI'S SYNDROME HERPESVIRUS PROTEASE AND ASSEMBLY PROTEIN COMPOSITIONS AND METHODS

[75] Inventors: Charles S. Craik, San Francisco; Ayçe Ünal, Sunnyvale; Donald E. Ganem, San Francisco, all of Calif.

[73] Assignee: The Regents of the University of California, Oakland, Calif.

[21] Appl. No.: 09/064,703

[22] Filed: Apr. 22, 1998

Related U.S. Application Data

[60] Provisional application No. 60/044,152, Apr. 22, 1997.

[51] Int. Cl.[7] .............................. C12N 9/64; C12N 9/50; C12N 15/00; C07H 21/04
[52] U.S. Cl. ..................... 435/226; 435/219; 435/320.1; 536/23.2
[58] Field of Search .................................. 435/69.1, 325, 435/320.1, 252.3, 194, 219, 226; 536/23.1, 23.2

[56] References Cited

FOREIGN PATENT DOCUMENTS

WO 96/14863  5/1996  WIPO.

OTHER PUBLICATIONS

Albrecht, J.C., et al., "Primary structure of the herpesvirus saimiri genome," J. Virol. 66:5047–5058 (1992).

Chang, Yuan, et al., "Identification of herpes–like DNA sequences in AIDS–associated Kaposi's sarcoma," Science 266:1865–1869 (1994).

Condra, J.H., et al., "In Vivo emergence of HIV–1 variants resistant to multiple protease inhibitors," Nature 374:569–571 (1995).

DiIanni, C.L., "Identification of the serine residue at the active site of the herpes simplex virustype 1 protease," J. Biol. Chem. 269:12672–12676 (1994).

Gao, M.L., et al., "The protease of herpes simplex virus type 1 is essential for functional capsid formation and viral growth," J. Virol. 68:3702–3712 (1994).

Gibson, Wade, et al., "Identification of precursor to cytomegalovirus capsid assembly protein and evidence the processing results in loss of its carboxy–terminal end," J. Virol. 64:1241–1249 (1990).

Gibson, Wade, et al., "Assemblin, a herpes virus serine maturational proteinase and new molecular target for antivirals," Perspect. Drug Discov. Desn. 2:413–426 (1994).

Liu, Fenyoung, and Bernard Roizman, "The herpes simplex virus 1 gene encoding a protease also contains within its coding domain the gene encoding the more abundant substrate," J. Virol. 65:5149–5156 (1991).

Loutsch, J.M., et al., "Cloning and sequence analysis of murine cytomegalovirus protease and capsid assembly protein genes," Biochem. Biophys. Res. Commun. 203:472–478 (1994).

Moore, P.S., et al., "Primary characterization of a herpesvirus agent associated with Kaposi's sarcoma," J. Virol. 70:549–558 (1996).

Perona, J.J., et al., "Structural basis of substrate specificity in the serine proteases," Protein Sci. 4:337–360 (1995).

Preston, V.G., "The herpes gene simplex virus gene UL26 proteinase in the presence of the UL26.5 gene product promotes the formation of the scaffold–like structures," J. Gen. Virol. 75:2355–2366 (1994).

Preston, V.G., "Processing of the herpes simplex virus assembly protein ICP35 near its carboxy terminal end requires the product of the whole of the UL26 reading frame," Virology 186:87–98 (1992).

Russo, J.J., et al., "Nucleotide sequence of the Kaposi sarcoma–associated herpesvirus (HHV8)," Proc. Natl. Acad. Sci, USA 93:14862–14867 (1996).

Ünal, A., et al., "The Protease and Assembly Protein of Kaposi's sarcoma–Associated Herpes Virus (Human Herpes Virus 8), " J. of Virol. 71(9):7030–7038 (1997).

Welch, A.R., et al., "A herpesvirus maturational proteinase, assemblin: identification of its gene, putative active site domain, and cleavage site," Proc. Natl. Acad. Sci. USA 88:10792–10796 (1991).

*Primary Examiner*—Ponnathapu Achutamurthy
*Assistant Examiner*—M. Monshipouri
*Attorney, Agent, or Firm*—Dehlinger & Associates

[57] ABSTRACT

Kaposi's Sarcoma Herpesvirus (KSHV) protease and assembly protein sequences are disclosed. Also disclosed are polynucleotides that encode the protease and assembly protein. The invention includes screening and detection methods, as well as KSHV protease inhibitory compositions.

13 Claims, 9 Drawing Sheets

```
ATG GCA CAG GGC CTG TAC GTC GGA GGG TTT GTA GAT GTT GTG TCC
TGC CCC AAG CTG GAG CAA GAG CTC TAT CTC GAT CCG GAT CAG GTG
ACG GAT TAT CTC CCA GTC ACA GAA CCC CTT CCA ATA ACA ATC GAA
CAC CTA CCA GAG ACA GAA GTG GGC TGG ACA CTG GGT CTA TTT CAA
GTG TCC CAC GGT ATT TTC TGC ACC GGA GCC ATC ACG TCG CCA GCC
TTC CTA GAG CTG GCA TCC AGG CTG GCG GAC ACC TCC CAC GTG GCC
AGA GCC CCC GTG AAA AAT CTC CCT AAG GAA CCA CTG TTG GAG ATA
CTC CAC ACG TGG CTC CCG GGG CTG TCT TTA TCG TCC ATA CAT CCC
CGC GAG TTA TCC CAG ACT CCC AGC GGT CCC GTG TTT CAA CAC GTA
TCA CTA TGC GCC CTG GGC GCC GA CGC GGC ACA GTG GCC GTG TAC
GGA CAC GAC GCC GAG TGG GTG GTT TCC AGA TTC TCA TCA GTA TCT
AAG TCG GAG CGC GCC CAC ATC CTC CAG CAC GTA AGT AGC TGC AGG
CTG GAG GAC CTT TCC ACA CCA AAT TTC GTC AGT CCC CTG GAG ACC
TTA ATG GCA AAA GCT ATA GAT GCC AGC TTC ATA CGG GAC CGC CTC
GAC CTA TTG AAA ACT GAC AGA GGT GTG GCC AGC ATA TTG AGC CCG
GTG TAT TTA AAG GCC AGC CAA TTC CCG GCC GGC ATC CAA GCC GTC
ACA CCA CCC AGA CCA GCC ATG AAC AGC TCT GGT CAA GAG GAT ATC
ATA TCC ATC CCC AAA TCC GCC TTC CTG AGC ATG CTA CAA AGC AGC
ATC GAT GGA ATG AAG ACC ACA GCG GCA AAA ATG TCA CAT ACA CTT
TCA GGG CCA GGC CTA ATG GGG TGT GGG GGC CAG ATG TTC CCC ACC
```

Fig. 2A

```
GAC CAT CAC CTA CCT TCG TAT GTT TCA AAC CCA GCG CCA CCA TAC GGC TAC
GCT TAC AAG AAC CCA TAC GAT CCA TGG TAT TAC TCG CCA CAG CTG CCT GGA
TAT AGG ACG GGG AAG CGC AAG CGC GGC GCA GAG GAC GAC GAA GGA CAC CTC
TTT CCA GGA GAG GAG CCG GCG TAT CAC AAG GAT ATC TTG TCC ATG TCA AAG
AAC ATA GCG GAA ATA CAG TCT GAA CTC AAA GAG ATG AAA CTG AAC GGT TGG
CAC GCA GGG CCA CCG CCG TCC TCC TCT GCA GCA GCA GCC GCA GTA GAT CCA
CAC TAC AGG CCC CAC GCC AAT TCA GCG GCC CCG TGT CAA TTC CCG ACA ATG
AAG GAG CAC GGA GGA ACC TAC GTA CAC CCA CCC ATT TAC GTG CAG GCG CCA
CAC GGT CAG TTC CAG CAA GCG GCG CCC ATC CTT TTT GCT CAG CCA CAT GTG
AGC CAC CCG CCA GTC TCT ACA GGA CTC GCG GTA GTT GGC GCA CCA CCC GCT
GAA CCC ACC CCC GCC TCC AGC ACG CAG AGC ATC CAA CAA CAG GCA CCG GAG
ACC ACG CAT ACA CCA TGC GCG GCG GTG GAG AAA GAC GCT CCT ACG CCG AAC
CCT ACA TCG AAC CGC CTT GAA GCC AGC AGT CGC TCT AGT CCA AAA TCT AAA
ATT CGC AAG ATG TTC TGC GAG GAG CTC
```

Fig. 2B

CAG CTT TTG GTT CCC TTT AGT GAG GGT TAA TTT CGA GCT TGG CGT TAT CAT
GGT CAT AGC TGT TTC CTG TGT GAA AAT GTT ATC CGC TCC CCA ATT CCC CCC
AAC ATT CGA

Fig. 2C

CTG CTG AAC AAG CAG

Fig. 2D

```
                    CD5
         MAQG [LYVGGFVDVVS] CPKLEQELYLDPDQVTDYLPV

CD2                          CD4
         TEP[LPITIEHLPETEVGWT] LGLFQVSH [GIFCTGAI

TS] PAFLELASRLADTSHVARAPVKNLPKEPLLEIL

CD3                        CD1
         HT [WLPGLSLSSIH] PRELSQTPSGP [VFQHVSLCALG

CD6
         RRRGTVAVY] GHDAEWVVSR [FSSV] SKSERAHILQHV

CD7
         SSCRLEDLSTPNFVSPLET [LMAKAIDASFIRDRLD

R-SITE
         LLKTDTGVASI] LSPA YLKA*SQFP
```

Fig. 3A

```
         SQFPVGIQAVTPPRPAMNSSGQEDIISIPKSAFLSMLQS

SIDGMKTTAAKMSHTLSGPGLMGCGGQMFPTDHHLPSYV

SNPAPPYGYAYKNPYDPWYYSPQLPGYRTGKRKRGAEDD

EGHLFPGEEPAYHKDILSMSKNIAEIQSELKEMKLNGWH

AGPPPSSSAAAAAVDPHYRPHANSAAPCQFPTMKEHGGT

YVHPPIYVQAPHGQFQQAAPILFAQPHVSHPPVSTGLAV

VGAPPAEPTPASSTQSIQQQAPETTHTPCAAVEKDAPTP

M-SITE                    EXT
         NPTSN [RLEA*SSRS] SPKSKIRKMFCEEL [LLNKQ]
```

Fig. 3B

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
        (A) LENGTH: 1590 base pairs
        (B) TYPE: nucleic acid
        (C) STRANDEDNESS: single
        (D) TOPOLOGY: linear (vii) IMMEDIATE SOURCE:
        (B) CLONE: KSHV Pr/AP polyprotein coding sequence (xi) SEQUENCE DESCRIPTION: SEQ ID NO:1:

```
ATGGCACAGG GCCTGTACGT CGGAGGGTTT GTAGATGTTG TGTCCTGCCC CAAGCTGGAG      60

CAAGAGCTCT ATCTCGATCC GGATCAGGTG ACGGATTATC TCCCAGTCAC AGAACCCCTT     120

CCAATAACAA TCGAACACCT ACCAGAGACA GAAGTGGGCT GGACACTGGG TCTATTTCAA     180

GTGTCCCACG GTATTTTCTG CACCGGAGCC ATCACGTCGC CAGCCTTCCT AGAGCTGGCA     240

TCCAGGCTGG CGGACACCTC CCACGTGGCC AGAGCCCCCG TGAAAAATCT CCCTAAGGAA     300

CCACTGTTGG AGATACTCCA CACGTGGCTC CCGGGGCTGT CTTTATCGTC CATACATCCC     360

CGCGAGTTAT CCCAGACTCC CAGCGGTCCC GTGTTTCAAC ACGTATCACT ATGCGCCCTG     420

GGGCGCCGAC GCGGCACAGT GGCCGTGTAC GGACACGACG CCGAGTGGGT GGTTTCCAGA     480

TTCTCATCAG TATCTAAGTC GGAGCGCGCC CACATCCTCC AGCACGTAAG TAGCTGCAGG     540

CTGGAGGACC TTTCCACACC AAATTTCGTC AGTCCCCTGG AGACCTTAAT GGCAAAAGCT     600

ATAGATGCCA GCTTCATACG GGACCGCCTC GACCTATTGA AAACTGACAG AGGTGTGGCC     660

AGCATATTGA GCCCGGTGTA TTTAAAGGCC AGCCAATTCC CGGCCGGCAT CCAAGCCGTC     720

ACACCACCCA GACCAGCCAT GAACAGCTCT GGTCAAGAGG ATATCATATC CATCCCCAAA     780

TCCGCCTTCC TGAGCATGCT ACAAAGCAGC ATCGATGGAA TGAAGACCAC AGCGGCAAAA     840

ATGTCACATA CACTTTCAGG GCCAGGCCTA ATGGGGTGTG GGGGCCAGAT GTTCCCCACC     900

GACCATCACC TACCTTCGTA TGTTTCAAAC CCAGCGCCAC CATACGGCTA CGCTTACAAG     960
```

```
AACCCATACG ATCCATGGTA TTACTCGCCA CAGCTGCCTG GATATAGGAC GGGGAAGCGC      1020

AAGCGCGGCG CAGAGGACGA CGAAGGACAC CTCTTTCCAG GAGAGGAGCC GGCGTATCAC      1080

AAGGATATCT TGTCCATGTC AAAGAACATA GCGGAAATAC AGTCTGAACT CAAAGAGATG      1140

AAACTGAACG GTTGGCACGC AGGGCCACCG CCGTCCTCCT CTGCAGCAGC AGCCGCAGTA      1200

GATCCACACT ACAGGCCCCA CGCCAATTCA GCGGCCCCGT GTCAATTCCC GACAATGAAG      1260

GAGCACGGAG GAACCTACGT ACACCCACCC ATTTACGTGC AGGCGCCACA CGGTCAGTTC      1320

CAGCAAGCGG CGCCCATCCT TTTTGCTCAG CCACATGTGA GCCACCCGCC AGTCTCTACA      1380

GGACTCGCGG TAGTTGGCGC ACCACCCGCT GAACCCACCC CCGCCTCCAG CACGCAGAGC      1440

ATCCAACAAC AGGCACCGGA GACCACGCAT ACACCATGCG CGGCGGTGGA GAAAGACGCT      1500

CCTACGCCGA ACCCTACATC GAACCGCCTT GAAGCCAGCA GTCGCTCTAG TCCAAAATCT      1560

AAAATTCGCA AGATGTTCTG CGAGGAGCTC                                      1590

(2) INFORMATION FOR SEQ ID NO:2:

(i) SEQUENCE CHARACTERISTICS:
          (A) LENGTH: 111 base pairs
          (B) TYPE: nucleic acid
          (C) STRANDEDNESS: single
          (D) TOPOLOGY: linear (vii) IMMEDIATE SOURCE:
          (B) CLONE: 3' extension of SEQ ID NO:1

(xi) SEQUENCE DESCRIPTION: SEQ ID NO:2:

CAGCTTTTGG TTCCCTTTAG TGAGGGTTAA TTTCGAGCTT GGCGTTATCA TGGTCATAGC        60

TGTTTCCTGT GTGAAAATGT TATCCGCTCC CCAATTCCCC CCAACATTCG A                111

(2) INFORMATION FOR SEQ ID NO:3:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (vii) IMMEDIATE SOURCE:
          (B) CLONE: 3' extension of SEQ ID NO:1

(xi) SEQUENCE DESCRIPTION: SEQ ID NO:3:

CTGCTGAACA AGCAG                                                         15

(2) INFORMATION FOR SEQ ID NO:4:

(i) SEQUENCE CHARACTERISTICS:
          (A) LENGTH: 1701 base pairs
          (B) TYPE: nucleic acid
          (C) STRANDEDNESS: single
          (D) TOPOLOGY: linear (vii) IMMEDIATE SOURCE:
          (B) CLONE: KSHV Pr/AP polyprotein including SEQ ID NO:2

(xi) SEQUENCE DESCRIPTION: SEQ ID NO:4:

ATGGCACAGG GCCTGTACGT CGGAGGGTTT GTAGATGTTG TGTCCTGCCC CAAGCTGGAG        60

CAAGAGCTCT ATCTCGATCC GGATCAGGTG ACGGATTATC TCCCAGTCAC AGAACCCCTT       120

CCAATAACAA TCGAACACCT ACCAGAGACA GAAGTGGGCT GGACACTGGG TCTATTTCAA       180

GTGTCCCACG GTATTTTCTG CACCGGAGCC ATCACGTCGC CAGCCTTCCT AGAGCTGGCA       240
```

-continued

```
TCCAGGCTGG CGGACACCTC CCACGTGGCC AGAGCCCCCG TGAAAAATCT CCCTAAGGAA      300

CCACTGTTGG AGATACTCCA CACGTGGCTC CCGGGGCTGT CTTTATCGTC CATACATCCC      360

CGCGAGTTAT CCCAGACTCC CAGCGGTCCC GTGTTTCAAC ACGTATCACT ATGCGCCCTG      420

GGGCGCCGAC GCGGCACAGT GGCCGTGTAC GGACACGACG CCGAGTGGGT GGTTTCCAGA      480

TTCTCATCAG TATCTAAGTC GGAGCGCGCC ACATCCTCC AGCACGTAAG TAGCTGCAGG       540

CTGGAGGACC TTTCCACACC AAATTTCGTC AGTCCCTGG AGACCTTAAT GGCAAAAGCT       600

ATAGATGCCA GCTTCATACG GGACCGCCTC GACCTATTGA AAACTGACAG AGGTGTGGCC      660

AGCATATTGA GCCCGGTGTA TTTAAAGGCC AGCCAATTCC CGGCCGGCAT CCAAGCCGTC      720

ACACCACCCA GACCAGCCAT GAACAGCTCT GGTCAAGAGG ATATCATATC CATCCCCAAA      780

TCCGCCTTCC TGAGCATGCT ACAAAGCAGC ATCGATGGAA TGAAGACCAC AGCGGCAAAA      840

ATGTCACATA CACTTTCAGG GCCAGGCCTA ATGGGGTGTG GGGCCAGAT GTTCCCCACC       900

GACCATCACC TACCTTCGTA TGTTTCAAAC CCAGCGCCAC CATACGGCTA CGCTTACAAG      960

AACCCATACG ATCCATGGTA TTACTCGCCA CAGCTGCCTG GATATAGGAC GGGGAAGCGC     1020

AAGCGCGGCG CAGAGGACGA CGAAGGACAC CTCTTTCCAG GAGAGGAGCC GGCGTATCAC     1080

AAGGATATCT TGTCCATGTC AAAGAACATA GCGGAAATAC AGTCTGAACT CAAAGAGATG     1140

AAACTGAACG GTTGGCACGC AGGGCCACCG CCGTCCTCCT CTGCAGCAGC AGCCGCAGTA     1200

GATCCACACT ACAGGCCCCA CGCCAATTCA GCGGCCCCGT GTCAATTCCC GACAATGAAG     1260

GAGCACGGAG GAACCTACGT ACACCCACCC ATTTACGTGC AGGCGCCACA CGGTCAGTTC     1320

CAGCAAGCGG CGCCCATCCT TTTTGCTCAG CCACATGTGA GCCACCCGCC AGTCTCTACA     1380

GGACTCGCGG TAGTTGGCGC ACCACCCGCT GAACCCACCC CCGCCTCCAG CACGCAGAGC     1440

ATCCAACAAC AGGCACCGGA GACCACGCAT ACACCATGCG CGGCGGTGGA GAAAGACGCT     1500

CCTACGCCGA ACCCTACATC GAACCGCCTT GAAGCCAGCA GTCGCTCTAG TCCAAAATCT     1560

AAAATTCGCA AGATGTTCTG CGAGGAGCTC CAGCTTTTGG TTCCCTTTAG TGAGGGTTAA     1620

TTTCGAGCTT GGCGTTATCA TGGTCATAGC TGTTTCCTGT GTGAAAATGT TATCCGCTCC     1680

CCAATTCCCC CCAACATTCG A                                               1701

(2) INFORMATION FOR SEQ ID NO:5:

(i) SEQUENCE CHARACTERISTICS:
        (A) LENGTH: 1605 base pairs
        (B) TYPE: nucleic acid
        (C) STRANDEDNESS: single
        (D) TOPOLOGY: linear (vii) IMMEDIATE SOURCE:
        (B) CLONE: KSHV Pr/AP polyprotein including SEQ ID NO:3

(xi) SEQUENCE DESCRIPTION: SEQ ID NO:5:

ATGGCACAGG GCCTGTACGT CGGAGGGTTT GTAGATGTTG TGTCCTGCCC CAAGCTGGAG       60

CAAGAGCTCT ATCTCGATCC GGATCAGGTG ACGGATTATC TCCCAGTCAC AGAACCCCTT      120

CCAATAACAA TCGAACACCT ACCAGAGACA GAAGTGGGCT GGACACTGGG TCTATTTCAA      180

GTGTCCCACG GTATTTTCTG CACCGGAGCC ATCACGTCGC CAGCCTTCCT AGAGCTGGCA      240

TCCAGGCTGG CGGACACCTC CCACGTGGCC AGAGCCCCCG TGAAAAATCT CCCTAAGGAA      300

CCACTGTTGG AGATACTCCA CACGTGGCTC CCGGGGCTGT CTTTATCGTC CATACATCCC      360

CGCGAGTTAT CCCAGACTCC CAGCGGTCCC GTGTTTCAAC ACGTATCACT ATGCGCCCTG      420

GGGCGCCGAC GCGGCACAGT GGCCGTGTAC GGACACGACG CCGAGTGGGT GGTTTCCAGA      480
```

```
TTCTCATCAG TATCTAAGTC GGAGCGCGCC CACATCCTCC AGCACGTAAG TAGCTGCAGG       540

CTGGAGGACC TTTCCACACC AAATTTCGTC AGTCCCCTGG AGACCTTAAT GGCAAAAGCT       600

ATAGATGCCA GCTTCATACG GGACCGCCTC GACCTATTGA AAACTGACAG AGGTGTGGCC       660

AGCATATTGA GCCCGGTGTA TTTAAAGGCC AGCCAATTCC CGGCCGGCAT CCAAGCCGTC       720

ACACCACCCA GACCAGCCAT GAACAGCTCT GGTCAAGAGG ATATCATATC CATCCCCAAA       780

TCCGCCTTCC TGAGCATGCT ACAAAGCAGC ATCGATGGAA TGAAGACCAC AGCGGCAAAA       840

ATGTCACATA CACTTTCAGG GCCAGGCCTA ATGGGGTGTG GGGGCCAGAT GTTCCCCACC       900

GACCATCACC TACCTTCGTA TGTTTCAAAC CCAGCGCCAC CATACGGCTA CGCTTACAAG       960

AACCCATACG ATCCATGGTA TTACTCGCCA CAGCTGCCTG GATATAGGAC GGGGAAGCGC      1020

AAGCGCGGCG CAGAGGACGA CGAAGGACAC CTCTTTCCAG GAGAGGAGCC GGCGTATCAC      1080

AAGGATATCT TGTCCATGTC AAAGAACATA GCGGAAATAC AGTCTGAACT CAAAGAGATG      1140

AAACTGAACG GTTGGCACGC AGGGCCACCG CCGTCCTCCT CTGCAGCAGC AGCCGCAGTA      1200

GATCCACACT ACAGGCCCCA CGCCAATTCA GCGGCCCCGT GTCAATTCCC GACAATGAAG      1260

GAGCACGGAG GAACCTACGT ACACCCACCC ATTTACGTGC AGGCGCCACA CGGTCAGTTC      1320

CAGCAAGCGG CGCCCATCCT TTTTGCTCAG CCACATGTGA GCCACCCGCC AGTCTCTACA      1380

GGACTCGCGG TAGTTGGCGC ACCACCCGCT GAACCCACCC CCGCCTCCAG CACGCAGAGC      1440

ATCCAACAAC AGGCACCGGA GACCACGCAT ACACCATGCG CGGCGGTGGA GAAAGACGCT      1500

CCTACGCCGA ACCCTACATC GAACCGCCTT GAAGCCAGCA GTCGCTCTAG TCCAAAATCT      1560

AAAATTCGCA AGATGTTCTG CGAGGAGCTC CTGCTGAACA AGCAG                     1605

(2) INFORMATION FOR SEQ ID NO:6:

(i) SEQUENCE CHARACTERISTICS:
         (A) LENGTH: 690 base pairs
         (B) TYPE: nucleic acid
         (C) STRANDEDNESS: single
         (D) TOPOLOGY: linear (vii) IMMEDIATE SOURCE:
         (B) CLONE: KSHV Pr coding sequence (xi) SEQUENCE DESCRIPTION: SEQ ID NO:6:

ATGGCACAGG GCCTGTACGT CGGAGGGTTT GTAGATGTTG TGTCCTGCCC CAAGCTGGAG        60

CAAGAGCTCT ATCTCGATCC GGATCAGGTG ACGGATTATC TCCCAGTCAC AGAACCCCTT       120

CCAATAACAA TCGAACACCT ACCAGAGACA GAAGTGGGCT GGACACTGGG TCTATTTCAA       180

GTGTCCCACG GTATTTTCTG CACCGGAGCC ATCACGTCGC CAGCCTTCCT AGAGCTGGCA       240

TCCAGGCTGG CGGACACCTC CCACGTGGCC AGAGCCCCCG TGAAAAATCT CCCTAAGGAA       300

CCACTGTTGG AGATACTCCA CACGTGGCTC CCGGGGCTGT CTTTATCGTC CATACATCCC       360

CGCGAGTTAT CCCAGACTCC CAGCGGTCCC GTGTTTCAAC ACGTATCACT ATGCGCCCTG       420

GGGCGCCGAC GCGGCACAGT GGCCGTGTAC GGACACGACG CCGAGTGGGT GGTTTCCAGA       480

TTCTCATCAG TATCTAAGTC GGAGCGCGCC CACATCCTCC AGCACGTAAG TAGCTGCAGG       540

CTGGAGGACC TTTCCACACC AAATTTCGTC AGTCCCCTGG AGACCTTAAT GGCAAAAGCT       600

ATAGATGCCA GCTTCATACG GGACCGCCTC GACCTATTGA AAACTGACAG AGGTGTGGCC       660

AGCATATTGA GCCCGGTGTA TTTAAAGGCC                                       690

(2) INFORMATION FOR SEQ ID NO:7:
```

(i) SEQUENCE CHARACTERISTICS:
     (A) LENGTH: 230 amino acids
     (B) TYPE: amino acid
     (D) TOPOLOGY: linear (ii) MOLECULE TYPE: protein (vii) IMMEDIATE SOURCE:
     (B) CLONE: KSHV Pr (xi) SEQUENCE DESCRIPTION: SEQ ID NO:7:

```
Met Ala Gln Gly Leu Tyr Val Gly Gly Phe Val Asp Val Ser Cys
  1               5                  10                  15

Pro Lys Leu Glu Gln Glu Leu Tyr Leu Asp Pro Asp Gln Val Thr Asp
             20                  25                  30

Tyr Leu Pro Val Thr Glu Pro Leu Pro Ile Thr Ile Glu His Leu Pro
             35                  40                  45

Glu Thr Glu Val Gly Trp Thr Leu Gly Leu Phe Gln Val Ser His Gly
 50                  55                  60

Ile Phe Cys Thr Gly Ala Ile Thr Ser Pro Ala Phe Leu Glu Leu Ala
 65                  70                  75                  80

Ser Arg Leu Ala Asp Thr Ser His Val Ala Arg Ala Pro Val Lys Asn
             85                  90                  95

Leu Pro Lys Glu Pro Leu Leu Glu Ile Leu His Thr Trp Leu Pro Gly
            100                 105                 110

Leu Ser Leu Ser Ser Ile His Pro Arg Glu Leu Ser Gln Thr Pro Ser
            115                 120                 125

Gly Pro Val Phe Gln His Val Ser Leu Cys Ala Leu Gly Arg Arg Arg
130                 135                 140

Gly Thr Val Ala Val Tyr Gly His Asp Ala Glu Trp Val Val Ser Arg
145                 150                 155                 160

Phe Ser Ser Val Ser Lys Ser Glu Arg Ala His Ile Leu Gln His Val
                165                 170                 175

Ser Ser Cys Arg Leu Glu Asp Leu Ser Thr Pro Asn Phe Val Ser Pro
            180                 185                 190

Leu Glu Thr Leu Met Ala Lys Ala Ile Asp Ala Ser Phe Ile Arg Asp
            195                 200                 205

Arg Leu Asp Leu Leu Lys Thr Asp Arg Gly Val Ala Ser Ile Leu Ser
210                 215                 220

Pro Val Tyr Leu Lys Ala
225                 230
```

(2) INFORMATION FOR SEQ ID NO:8:

(i) SEQUENCE CHARACTERISTICS:
          (A) LENGTH: 900 base pairs
          (B) TYPE: nucleic acid
          (C) STRANDEDNESS: single
          (D) TOPOLOGY: linear (vii) IMMEDIATE SOURCE:
          (B) CLONE: KSHV AP coding sequence (xi) SEQUENCE DESCRIPTION: SEQ ID NO:8:

```
AGCCAATTCC CGGCCGGCAT CCAAGCCGTC ACACCACCCA GACCAGCCAT GAACAGCTCT    60

GGTCAAGAGG ATATCATATC CATCCCCAAA TCCGCCTTCC TGAGCATGCT ACAAAGCAGC   120

ATCGATGGAA TGAAGACCAC AGCGGCAAAA ATGTCACATA CACTTTCAGG GCCAGGCCTA   180

ATGGGGTGTG GGGGCCAGAT GTTCCCCACC GACCATCACC TACCTTCGTA TGTTTCAAAC   240
```

```
CCAGCGCCAC CATACGGCTA CGCTTACAAG AACCCATACG ATCCATGGTA TTACTCGCCA      300

CAGCTGCCTG GATATAGGAC GGGGAAGCGC AAGCGCGGCG CAGAGGACGA CGAAGGACAC      360

CTCTTTCCAG GAGAGGAGCC GGCGTATCAC AAGGATATCT TGTCCATGTC AAAGAACATA      420

GCGGAAATAC AGTCTGAACT CAAAGAGATG AAACTGAACG GTTGGCACGC AGGGCCACCG      480

CCGTCCTCCT CTGCAGCAGC AGCCGCAGTA GATCCACACT ACAGGCCCCA CGCCAATTCA      540

GCGGCCCCGT GTCAATTCCC GACAATGAAG GAGCACGGAG GAACCTACGT ACACCCACCC      600

ATTTACGTGC AGGCGCCACA CGGTCAGTTC CAGCAAGCGG CGCCCATCCT TTTTGCTCAG      660

CCACATGTGA GCCACCCGCC AGTCTCTACA GGACTCGCGG TAGTTGGCGC ACCACCCGCT      720

GAACCCACCC CCGCCTCCAG CACGCAGAGC ATCCAACAAC AGGCACCGGA GACCACGCAT      780

ACACCATGCG CGGCGGTGGA GAAAGACGCT CCTACGCCGA ACCCTACATC GAACCGCCTT      840

GAAGCCAGCA GTCGCTCTAG TCCAAAATCT AAAATTCGCA AGATGTTCTG CGAGGAGCTC      900
```

(2) INFORMATION FOR SEQ ID NO:9:

(i) SEQUENCE CHARACTERISTICS:
        (A) LENGTH: 915 base pairs
        (B) TYPE: nucleic acid
        (C) STRANDEDNESS: single
        (D) TOPOLOGY: linear (vii) IMMEDIATE SOURCE:
        (B) CLONE: KSHV AP coding sequence including SEQ ID NO:3

(xi) SEQUENCE DESCRIPTION: SEQ ID NO:9:

```
AGCCAATTCC CGGCCGGCAT CCAAGCCGTC ACACCACCCA GACCAGCCAT GAACAGCTCT       60

GGTCAAGAGG ATATCATATC CATCCCCAAA TCCGCCTTCC TGAGCATGCT ACAAAGCAGC      120

ATCGATGGAA TGAAGACCAC AGCGGCAAAA ATGTCACATA CACTTTCAGG GCCAGGCCTA      180

ATGGGGTGTG GGGGCCAGAT GTTCCCCACC GACCATCACC TACCTTCGTA TGTTTCAAAC      240

CCAGCGCCAC CATACGGCTA CGCTTACAAG AACCCATACG ATCCATGGTA TTACTCGCCA      300

CAGCTGCCTG GATATAGGAC GGGGAAGCGC AAGCGCGGCG CAGAGGACGA CGAAGGACAC      360

CTCTTTCCAG GAGAGGAGCC GGCGTATCAC AAGGATATCT TGTCCATGTC AAAGAACATA      420

GCGGAAATAC AGTCTGAACT CAAAGAGATG AAACTGAACG GTTGGCACGC AGGGCCACCG      480

CCGTCCTCCT CTGCAGCAGC AGCCGCAGTA GATCCACACT ACAGGCCCCA CGCCAATTCA      540

GCGGCCCCGT GTCAATTCCC GACAATGAAG GAGCACGGAG GAACCTACGT ACACCCACCC      600

ATTTACGTGC AGGCGCCACA CGGTCAGTTC CAGCAAGCGG CGCCCATCCT TTTTGCTCAG      660

CCACATGTGA GCCACCCGCC AGTCTCTACA GGACTCGCGG TAGTTGGCGC ACCACCCGCT      720

GAACCCACCC CCGCCTCCAG CACGCAGAGC ATCCAACAAC AGGCACCGGA GACCACGCAT      780

ACACCATGCG CGGCGGTGGA GAAAGACGCT CCTACGCCGA ACCCTACATC GAACCGCCTT      840

GAAGCCAGCA GTCGCTCTAG TCCAAAATCT AAAATTCGCA AGATGTTCTG CGAGGAGCTC      900

CTGCTGAACA AGCAG                                                      915
```

(2) INFORMATION FOR SEQ ID NO:10:

(i) SEQUENCE CHARACTERISTICS:
        (A) LENGTH: 300 amino acids
        (B) TYPE: amino acid
        (D) TOPOLOGY: linear (ii) MOLECULE TYPE: protein

```
    (vii) IMMEDIATE SOURCE:
          (B) CLONE: KSHV AP encoded by SEQ ID NO:8

(xi) SEQUENCE DESCRIPTION: SEQ ID NO:10:

Ser Gln Phe Pro Ala Gly Ile Gln Ala Val Thr Pro Pro Arg Pro Ala
1               5                  10                 15

Met Asn Ser Ser Gly Gln Glu Asp Ile Ile Ser Ile Pro Lys Ser Ala
            20                  25                  30

Phe Leu Ser Met Leu Gln Ser Ser Ile Asp Gly Met Lys Thr Thr Ala
            35                  40                  45

Ala Lys Met Ser His Thr Leu Ser Gly Pro Gly Leu Met Gly Cys Gly
50              55                  60

Gly Gln Met Phe Pro Thr Asp His His Leu Pro Ser Tyr Val Ser Asn
65                  70                  75                  80

Pro Ala Pro Pro Tyr Gly Tyr Ala Tyr Lys Asn Pro Tyr Asp Pro Trp
                85                  90                  95

Tyr Tyr Ser Pro Gln Leu Pro Gly Tyr Arg Thr Gly Lys Arg Lys Arg
                100                 105                 110

Gly Ala Glu Asp Asp Glu Gly His Leu Phe Pro Gly Glu Pro Ala
            115                 120                 125

Tyr His Lys Asp Ile Leu Ser Met Ser Lys Asn Ile Ala Glu Ile Gln
130                 135                 140

Ser Glu Leu Lys Glu Met Lys Leu Asn Gly Trp His Ala Gly Pro Pro
145                 150                 155                 160

Pro Ser Ser Ser Ala Ala Ala Ala Val Asp Pro His Tyr Arg Pro
                165                 170                 175

His Ala Asn Ser Ala Ala Pro Cys Gln Phe Pro Thr Met Lys Glu His
            180                 185                 190

Gly Gly Thr Tyr Val His Pro Pro Ile Tyr Val Gln Ala Pro His Gly
                195                 200                 205

Gln Phe Gln Gln Ala Ala Pro Ile Leu Phe Ala Gln Pro His Val Ser
210                 215                 220

His Pro Pro Val Ser Thr Gly Leu Ala Val Val Gly Ala Pro Pro Ala
225                 230                 235                 240

Glu Pro Thr Pro Ala Ser Ser Thr Gln Ser Ile Gln Gln Ala Pro
                245                 250                 255

Glu Thr Thr His Thr Pro Cys Ala Ala Val Glu Lys Asp Ala Pro Thr
            260                 265                 270

Pro Asn Pro Thr Ser Asn Arg Leu Glu Ala Ser Ser Arg Ser Ser Pro
            275                 280                 285

Lys Ser Lys Ile Arg Lys Met Phe Cys Glu Glu Leu
290                 295                 300

(2) INFORMATION FOR SEQ ID NO:11:

(i) SEQUENCE CHARACTERISTICS:
        (A) LENGTH: 305 amino acids
        (B) TYPE: amino acid
        (D) TOPOLOGY: linear (ii) MOLECULE TYPE: protein (vii) IMMEDIATE SOURCE:
          (B) CLONE: KSHV AP encoded by SEQ ID NO:9

(xi) SEQUENCE DESCRIPTION: SEQ ID NO:11:

Ser Gln Phe Pro Ala Gly Ile Gln Ala Val Thr Pro Pro Arg Pro Ala
1               5                  10                 15
```

```
Met Asn Ser Ser Gly Gln Glu Asp Ile Ile Ser Ile Pro Lys Ser Ala
              20                  25                  30

Phe Leu Ser Met Leu Gln Ser Ser Ile Asp Gly Met Lys Thr Thr Ala
              35                  40                  45

Ala Lys Met Ser His Thr Leu Ser Gly Pro Gly Leu Met Gly Cys Gly
          50                  55                  60

Gly Gln Met Phe Pro Thr Asp His His Leu Pro Ser Tyr Val Ser Asn
65                  70                  75                  80

Pro Ala Pro Pro Tyr Gly Tyr Ala Tyr Lys Asn Pro Tyr Asp Pro Trp
                  85                  90                  95

Tyr Tyr Ser Pro Gln Leu Pro Gly Tyr Arg Thr Gly Lys Arg Lys Arg
                 100                 105                 110

Gly Ala Glu Asp Asp Glu Gly His Leu Phe Pro Gly Glu Glu Pro Ala
             115                 120                 125

Tyr His Lys Asp Ile Leu Ser Met Ser Lys Asn Ile Ala Glu Ile Gln
         130                 135                 140

Ser Glu Leu Lys Glu Met Lys Leu Asn Gly Trp His Ala Gly Pro Pro
145                 150                 155                 160

Pro Ser Ser Ala Ala Ala Ala Val Asp Pro His Tyr Arg Pro
                 165                 170                 175

His Ala Asn Ser Ala Ala Pro Cys Gln Phe Pro Thr Met Lys Glu His
                 180                 185                 190

Gly Gly Thr Tyr Val His Pro Pro Ile Tyr Val Gln Ala Pro His Gly
             195                 200                 205

Gln Phe Gln Gln Ala Ala Pro Ile Leu Phe Ala Gln Pro His Val Ser
         210                 215                 220

His Pro Pro Val Ser Thr Gly Leu Ala Val Val Gly Ala Pro Pro Ala
225                 230                 235                 240

Glu Pro Thr Pro Ala Ser Ser Thr Gln Ser Ile Gln Gln Ala Pro
                 245                 250                 255

Glu Thr Thr His Thr Pro Cys Ala Ala Val Glu Lys Asp Ala Pro Thr
             260                 265                 270

Pro Asn Pro Thr Ser Asn Arg Leu Glu Ala Ser Ser Arg Ser Ser Pro
         275                 280                 285

Lys Ser Lys Ile Arg Lys Met Phe Cys Glu Glu Leu Leu Asn Lys
        290                 295                 300

Gln
305

(2) INFORMATION FOR SEQ ID NO:12:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (vii) IMMEDIATE SOURCE:
        (B) CLONE: KSHV R-site (xi) SEQUENCE DESCRIPTION: SEQ ID NO:12:

Tyr Leu Lys Ala Ser Gln Phe Pro
1               5
```

(2) INFORMATION FOR SEQ ID NO:13:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (vii) IMMEDIATE SOURCE:
        (B) CLONE: KSHV M-site (xi) SEQUENCE DESCRIPTION: SEQ ID NO:13:

Arg Leu Glu Ala Ser Ser Arg Ser
1               5

(2) INFORMATION FOR SEQ ID NO:14:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (vii) IMMEDIATE SOURCE:
        (B) CLONE: KSHV Pr dimer interface (xi) SEQUENCE DESCRIPTION: SEQ ID NO:14:

Pro Leu Glu Thr Leu Met Ala Lys Ala Ile Asp Ala Ser Phe
1               5                   10

(2) INFORMATION FOR SEQ ID NO:15:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (vii) IMMEDIATE SOURCE:
        (B) CLONE: HCMV M-site (xi) SEQUENCE DESCRIPTION: SEQ ID NO:15:

Arg Gly Val Val Asn Ala Ser Ser Arg Leu Ala
1               5                   10

(2) INFORMATION FOR SEQ ID NO:16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:16:

GGGGGTCCGG ACAGGGCCTG TACGTCGGA                                29

(2) INFORMATION FOR SEQ ID NO:17:

(i) SEQUENCE CHARACTERISTICS:
        (A) LENGTH: 32 base pairs
        (B) TYPE: nucleic acid
        (C) STRANDEDNESS: single -continued (D) TOPOLOGY: linear (xi) SEQUENCE DESCRIPTION: SEQ ID NO:17:

GGGGGAAGCT TCTAGGCCTT TAAATACACC GG                                32

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:18:

CTCCCGGGGC TGGCCTTATC GTCCATAC                                     28

(2) INFORMATION FOR SEQ ID NO:19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:19:

TATGGACGAT AAGGCCAGCC CCGGGAG                                      27

KAPOSI'S SYNDROME HERPESVIRUS PROTEASE AND ASSEMBLY PROTEIN COMPOSITIONS AND METHODS

This application claims the priority of U.S. Provisional Application No. 60/044,152 filed Apr. 22, 1997, which is incorporated herein by reference.

This invention was made with Government support under Grant No. GM39552, awarded by the National Institutes of Health. The Government has certain rights in this invention.

FIELD OF THE INVENTION

The present invention relates to polypeptide and nucleotide compositions derived from Kaposi's Syndrome Herpesvirus (KSHV). Such compositions are particularly useful for use in therapeutics, drug screening, and test kits for diagnosing and determining patient status with respect to KSHV.

REFERENCES

Ambroziak, J. A., et al., *Science* 268:582–583 (1995).
Ausubel, F. M., et al., in *CURRENT PROTOCOLS IN MOLECULAR BIOLOGY*, Wiley & Sons, New York, N.Y. (1990).
Banga, A. K., in *THERAPEUTIC PEPTIDES AND PROTEINS*, Technomic Publishing Co., Inc., Lancaster, Pa. (1995).
Boshoff, C., et al., *Nat. Med.* 1:1274–1278 (1995).
Chang, Y., et al., *Science* 266:1865–1869 (1994).
Chuck, S., et al., *J. Infect. Dis.* 173:248–251 (1996).
Craik, C. S., et al., *Science* 237:909–913 (1987).
Dayhoff, M. O., in *ATLAS OF PROTEIN SEQUENCE AND STRUCTURE* Vol. 5, National Biomedical Research Foundation, pp. 101–110, and Supplement 2 to this volume, pp. 1–10 (1972).
Desai, et al., *J. Virol.* 68:5365–5374 (1994).
DesJarlais, R. L., et al., *Proc. Natl. Acad. Sci. USA* 87(17):6644–8 (1990).
Evnin, L. B., et al., *Proc. Natl. Acad. Sci. USA* 87:6659–6663 (1990).
Gao, M., et al., *J. Virol.* 68:3702–3712 (1994).
Gao, M., et al., *Nat. Med.* 2:925–928 (1996).
Gennaro, A. R., Ed., *REMINGTON'S PHARMACEUTICAL SCIENCES* (18th Ed., Mack Publishing Co., Easton Pa. (1990)).
Gibson, W., *Virology* 111:516–537 (1981).
Gibson, W., and Roizman, B., *J. Virol.* 10:1044–1052 (1972).
Holskin, B. P., et al., *Anal. Biochem.* 227:148–155 (1995).
Hong, Z., et al., *J. Virol.* 70:533–540 (1996).
Huang, Y. Q., et al., *Lancet* 345:759–761 (1995).
Irmiere, A., and Gibson, W., *J. Virol.* 56:277–283 (1985).
Kedes, D. H., et al., *Nat. Med.* 2:918–924 (1996).
Kettner, C., et al., *Meth. Enzymol.* 80(PT.C):826–846 (1981).
Liu, F. Y., and Roizman, B., *J. Virol.* 65:5149–5156 (1991).
Long, E. O., et al., *Hum. Immunol.*, 31(4):229–235 (1991).
Loutsch, J. M., et al., *Biochem. Biophys. Res. Commun.* 203:472–478 (1994).
Moore, P. S., and Chang, Y., *N. Engl. J. Med.* 332:1181–1185 (1995).
Moore, P. S., et al., *AIDS* 10: 175–180 (1995).
O'Callaghan, D. J., and Randall, C. C., *Prog. Med. Virol.* 22:152–210 (1976).
Preston, V. G., et al., *J. Virol.* 45:1056–1064 (1983).
Preston, V. G., et al., *Virology* 186:87–98 (1992).
Preston, V. G., et al., *J. Gen. Virol.* 75:2355–2366 (1994).
Renne, R., et al., *Nat. Med.* 2:342–346 (1996).
Rixon, F. J., et al., *J. Gen. Virol.* 69:2879–2891 (1988).
Russo, J. J., et al., *Proc. Natl. Acad. Sci. USA* 93:14862–14867 (1996).
Salto, R. et al., *J. Biol. Chem.* 269(14):10691–10698 (1994)
Schalling, M., et al., *Nat. Med.* 1:705–706 (1995).
Sherman, G., and Bachenheimer, S. L., *Virology* 163:471–480 (1988).
Soulier, J., et al., *Blood* 86:1276–1280 (1995).
Thomsen, D. R., et al., *J. Virol.* 68:2442–2457 (1994).
Welch, A. R., et al., *Proc. Natl. Acad. Sci. USA* 88:10792–10796 (1991).
Wood, L. J., et al., *J. Virol.* 71:179–190 (1997).
Yu, Z., et al., *J. Amer. Chem. Soc.* 118:5846–5856 (1996).

BACKGROUND OF THE INVENTION

Kaposi's sarcoma (KS), once considered a rare tumor largely confined to elderly Mediterranean and African men, has recently re-emerged as the most common neoplasm of patients with the acquired immunodeficiency syndrome (AIDS): 15–25% of such patients will develop this tumor in the course of their human immunodeficiency virus (HIV) infection. While HIV infection is an important risk factor in KS development, studies indicate that it is not sufficient to explain the etiology of the disease. For example, KS is far more prevalent in AIDS patients who acquire their HIV infection by sexual routes than in those who contract HIV by percutaneous inoculation or vertical transmission. These findings suggest that a second, sexually transmitted cofactor may be required for KS development.

Recently, DNA sequences of a novel human herpesvirus (KS-associated herpesvirus, KSHV; also called human herpesvirus 8) have been identified in KS tumors. A growing body of evidence suggests an important role for this virus in KS pathogenesis: (i) infection precedes tumorigenesis and is associated with a striking increase in the risk of subsequent KS development (Moore, et al., 1995) (ii) the distribution of infection among HIV-positive patients parallels known KS risk (Gao, et al., 1996; Kedes, et al., 1996); (iii) all forms of KS, whether HIV-positive or HIV-negative, are strongly associated with KSHV infection (Ambroziak, et al., 1996; Chang, et al., 1994; Chuck, et al., 1996; Huang, et al., 1995; Moore and Chang 1995; Schalling, et al., 1995; Soulier, et al., 1995) and (iv) infection is targeted to the endothelial (spindle) cells, thought to be central to KS pathogenesis (Boshoff, et al., 1995). These findings suggest that prevention or suppression of KSHV infection could reduce the risk of KS development.

The identity of the KSHV protease molecule, activity and inhibitor specificity have been heretofore unknown. The present invention reveals cloning, expression and purification of the KSHV protease (Pr), which, surprisingly, has less than 60% sequence identity with any of the known members of the herpes virus family. Also forming part of the present invention is the characterization of the enzymatic activity of KSHV protease. These discoveries form the basis for screening assays and biochemical substrate inhibitors that can be used to treat Kaposi's Sarcoma according to the treatment methods described herein.

SUMMARY OF THE INVENTION

The invention is concerned with Kaposi's Sarcoma herpesvirus (KSHV) protease and assembly protein and the KSHV Pr/AP precursor. In one aspect the invention includes an isolated KSHV Pr/AP polypeptide having at least 70% sequence identity, preferably at least 80% identity, and more preferably at least 90% identity, to a polypeptide selected from the group consisting of SEQ ID NO:7, SEQ ID NO:10, SEQ ID NO:11, SEQ ID NO:12, SEQ ID NO:13, and SEQ ID NO:14.

In one embodiment the polypeptide corresponds to a KSHV protease having at least 70% sequence identity to the sequence identified as SEQ ID NO:7. In a further embodiment the protease sequence contains the non-variant amino acid positions His-46, Ser-114, His-134, Arg-142, and Arg-143, as found in the sequence SEQ ID NO:7. In another embodiment, the KSHV protease sequence includes one or more sequence regions corresponding to constant domain (CD) regions CD1–CD7 having the sequences shown in FIG. 3A. In another embodiment, the protease has the sequence identified as SEQ ID NO:7.

The invention further includes an isolated polynucleotide which encodes a polypeptide having at least 70%, preferably at least 80%, and more preferably at least 90%, sequence identity to a sequence selected from the group SEQ ID NO:7, SEQ ID NO:10, SEQ ID NO:11, SEQ ID NO:12, SEQ ID NO:13, and SEQ ID NO:14. In one embodiment, such a polynucleotide has the sequence identified as SEQ ID NO:6, SEQ ID NO:8, or SEQ ID NO:9. Such polynucleotides have a number of utilities contemplated by the invention, including, but not limited to, use in producing the polypeptides of the invention.

In related aspects, the invention also includes expression vectors that contain the various polynucleotides defined above, and host cells which contain these expression vectors.

The invention also provides a method for producing the polypeptides defined above, the method including the steps of (a) culturing the host cell containing an expression vector containing a polynucleotide defined above under conditions suitable for expression of the polypeptide, and (b) recovering the polypeptide from the host cell or cell culture media.

In another related aspect, the invention includes a method of identifying a compound which inhibits the isolated KSHV protease described above, comprising the steps of (a) incubating together the KSHV protease and a KSHV protease substrate, under conditions which allow the protease-mediated cleavage of the substrate, in the absence of a test compound, (b) measuring the extent of protease-mediated cleavage of the substrate in the absence of the test compound; (c) incubating together the KSHV protease and the KSHV protease substrate, under conditions which allow the protease-mediated cleavage of the substrate, in the presence of the test compound, (d) measuring the extent of protease-mediated cleavage of the substrate in the presence of the test compound; and (e) identifying the test compound as a KSHV protease inhibitor if the extent of protease-mediated cleavage of the substrate in the presence of the test compound is substantially less than the extent of protease-mediated cleavage of the substrate in the absence of the test compound, and if said test compound inhibits KSHV protease at an inhibitory concentration that is no more than 10 times an inhibitory concentration of the inhibitor peptide having the sequence Boc-YLKA-COCH$_2$Cl. In a preferred embodiment, the test compound is selected from a peptide combinatorial library.

In a related aspect, the invention includes a pharmaceutical composition comprising the KSHV protease inhibitor identified by the method described together with a suitable pharmaceutical carrier.

In still another related aspect, the invention includes a method of treating infection by KSHV. The method includes administering to a subject in need of such treatment an effective amount of the pharmaceutical composition containing a KSHV protease inhibitor as described above.

In another related aspect, the invention includes a method of treating a subject having Kaposi's sarcoma. The method includes administering an effective amount of a KSHV protease inhibitor as described above. In one embodiment, the treatment method includes further administering an effective amount of a second anti-viral compound, such as an antiviral compound that is effective to inhibit replication of human immunodeficiency virus (HIV). In a preferred embodiment, the second antiviral compound is selected from the group: zidovudine (AZT), ribavirin, indinavir, saquinavir, ritonavir and nelfinavir. In another preferred embodiment, the antiviral agent is selected from the group: acyclovir, ganciclovir, adenine arabinoside (Ara-A, vidarabine) and foscarnet. In still another preferred embodiment, the antiviral agent is selected from the group: amantadine, rimantadine, ribavirin and gamma-interferon.

These and other objects and features of the invention will become more fully apparent when the following detailed description of the invention is read in conjunction with the accompanying drawings.

BRIEF DESCRIPTION OF THE FIGURES

FIGS. 2A–2B show the DNA sequence, identified as SEQ ID NO:1, which encodes the KSHV PR/AP polyprotein which comprises the protease (KSHV Pr) and assembly protein (AP), where an arrow denotes the boundary between the KSHV Pr coding region (identified as SEQ ID NO:6), which ends at nt 690, and the AP coding region, which extends from nt 691 to the end (SEQ ID NO:8);

FIGS. 2C and 2D show two alternative 3' polynucleotide extensions of SEQ ID NO:1, designated SEQ ID NO:2 (FIG. 2C) and SEQ ID NO:3 (FIG. 2D), which, taken together with SEQ ID NO:1, produce SEQ ID NO:4 and SEQ ID NO:5, respectively;

FIG. 3A shows the deduced amino acid sequence of a KSHV protease (SEQ ID NO:7), with essential residues in bold type, conserved domain (CD) regions indicated as CD5, CD2, CD4, CD3, CD1, CD6, and CD7, together with the R-Site, in accordance with standard herpesvirus terminology;

FIG. 3B shows the deduced amino acid sequence of the assembly protein (AP; SEQ ID NO:10) showing the maturation site (M-site), along with a C-terminal peptide extension (EXT) encoded by SEQ ID NO:3, the peptide extension which, taken together with SEQ ID NO:10, forms the AP polypeptide sequence identified as SEQ ID NO:11;

BRIEF DESCRIPTION OF THE SEQUENCES

Figure 1:
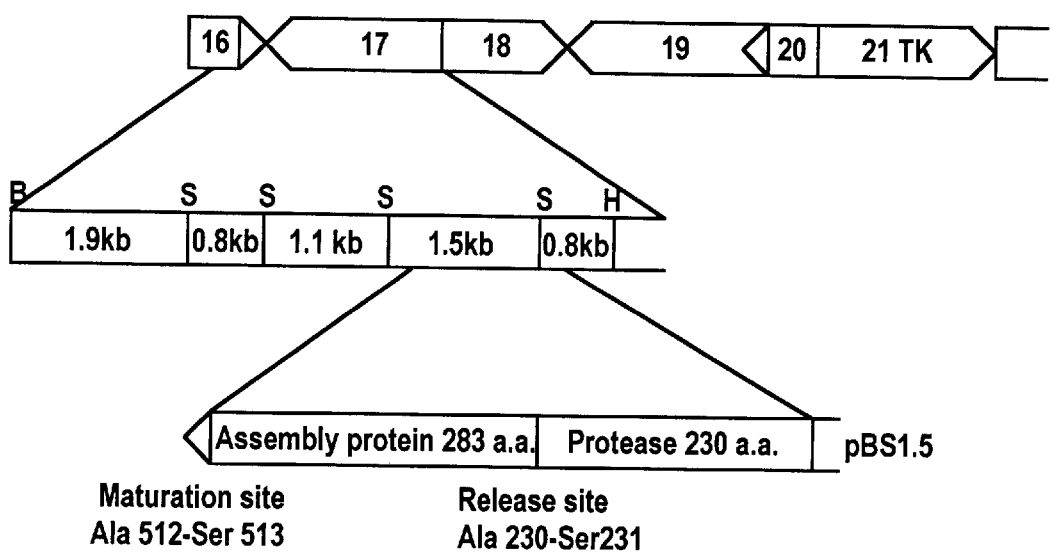
FIG. 1 shows a schematic of partial genome of KSHV and location of open reading frame (ORF) 17, where arrowheads denote the direction of transcription, and the following abbreviations are used: TK: Thymidine kinase, B: BamHI, S: SacI and H: HindIII.

SEQ ID NO:1 is a nucleic acid sequence which encodes a KSHV Pr/AP polyprotein;

SEQ ID NO:2 is a 3' polynucleotide extension of SEQ ID NO: 1;

SEQ ID NO:3 is another 3' polynucleotide extension of SEQ ID NO: 1;

SEQ ID NO:4 is a nucleic acid sequence encoding a KSHV Pr/AP polyprotein (SEQ ID NO:1) which further includes the 3' extension SEQ ID NO:2;

SEQ ID NO:5 is a nucleic acid sequence encoding a KSHV Pr/AP polyprotein (SEQ ID NO:1) which further includes the 3' extension SEQ ID NO:3;

SEQ ID NO:6 is a coding sequence for a KSHV protease (Pr);

SEQ ID NO:7 is the amino acid sequence of KSHV Pr encoded by SEQ ID NO:6;

SEQ ID NO:8 is a coding sequence for a KSHV assembly protein (AP);

SEQ ID NO:9 is a coding sequence for a KSHV AP which further includes the 3' extension SEQ ID NO:3;

SEQ ID NO:10 is the amino acid sequence of KSHV AP encoded by SEQ ID NO:8;

SEQ ID NO:11 is the amino acid sequence of KSHV AP encoded by SEQ ID NO:9;

SEQ ID NO:12 is a KSHV R-site peptide sequence;

SEQ ID NO:13 is a KSHV M-site peptide sequence;

SEQ ID NO:14 is a dimerization sequence of a KSHV Pr;

SEQ ID NO:15 is an HCMV M-site peptide sequence;

SEQ ID NO:16 is an oligonucleotide primer used in construction of the vector of Example 2;

SEQ ID NO:17 is another oligonucleotide primer used in construction of the vector of Example 2;

SEQ ID NO:18 is a mutagenic oligonucleotide used to prepare the Pr(S114A) mutant; and SEQ ID NO:19 is another mutagenic oligonucleotide used to prepare the Pr(S114A) mutant.

DETAILED DESCRIPTION OF THE INVENTION

I. Definitions

The term "polynucleotide" as used herein refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded RNA and DNA, and backbone modifications thereof, for example, methylphosphonate linkages. The term refers to deoxyribonucleic acids (DNA) as well as ribonucleic acids (RNA).

As used herein, the terms "substantial homology" or "substantial identity", and declinations thereof, refer to concordance of an amino acid sequence with another amino acid sequence or of a polynucleotide sequence with another polynucleotide sequence of at least 70% and preferably, at least 80%, and more preferably, at least 90%, when such sequences are arranged in a best fit alignment. In the case of nucleotide sequences, the terms also imply that the nucleotide sequence in question is capable of being detected in a screening assay by a hybridization probe derived from the nucleotide sequence defined as SEQ ID NO:1 under high stringency hybridization conditions.

The term "vector" refers to a nucleotide sequence that can assimilate new nucleic acids, and propagate those new sequences in an appropriate host. Vectors include, but are not limited to recombinant plasmids and viruses. The vector (e.g., plasmid or recombinant virus) comprising the nucleic acid of the invention can be in a carrier, for example, a plasmid complexed to protein, a plasmid complexed with lipid-based nucleic acid transduction systems, or other non-viral carrier systems.

The term "probe" as used herein refers to a structure comprised of a polynucleotide, as defined above, which contains a nucleic acid sequence complementary to a nucleic acid sequence present in the target molecule. The polynucleotide regions of probes may be composed of DNA, and/or RNA, and/or synthetic nucleotide analogs such as branched DNA (bDNA).

The term "high stringency" as used herein refers to nucleic acid hybridization conditions that allow sequences of a particular target sequence to basepair or bind specifically to a probe polynucleotide, when such target and probe contain at least about 70%, preferably at least about 80%, and more preferably at least about 90% nucleic acid sequence identity over the length of the probe polynucleotide.

The term "polypeptide" as used herein refers to a compound made up of a single chain of amino acid residues linked by peptide bonds. The term "protein" may be synonymous with the term "polypeptide" or may refer, in addition, to a complex of two or more polypeptides.

Amino acid residues are referred to herein by their standard single- or three-letter notations: A, ala, alanine; C, cys, cysteine; D, asp, aspartic acid; E, glu, glutamic acid; F, phe, phenylalanine; G, gly, glycine; H, his, histidine; I, ile, isoleucine; K, lys, lysine; L, leu, leucine; M, met, methionine; N, asn, asparagine; P, pro, proline; Q, gln, glutamine; R, arg, arginine; S, ser, serine; T, thr, threonine; V, val, valine; W, trp, tryptophan; X, hyp, hydroxyproline; Y, tyr, tyrosine.

Additional definitions of terms may be found in the text or may be inferred from the context in which the term is used.

II. Kaposi's Sarcoma Herpes Virus (KSHV) Protease Gene and Polypeptide Compositions KSHV has now been characterized as a herpesvirus. Although the KSHV protease revealed herein has a relatively low sequence identity with known herpes viruses (highest sequence identity with Herpesvirus saimiri, 56%), it shares certain characteristics with these viruses.

Herpesviruses mature through a common assembly pathway, which has been characterized in herpes simplex virus (HSV). Viral capsids assemble in the nucleus late in infection. Immature capsids lack DNA but contain an abundant internal polypeptide, the assembly protein (AP), that is not found in the mature, DNA-containing particles (Gibson, et al., 1991; Gibson and Roizman 1972; Irmiere and Gibson, 1985; O'Callaghan and Randall, 1976; Rixon, et al., 1988). This protein is known to interact with the major capsid protein (MCP) (Hong, et al., 1996; Wood, et al., 1997) This interaction is required for nuclear transport of the MCP and has also been proposed to act as a scaffold to facilitate the assembly of the capsid shell.

Following immature capsid assembly, the AP undergoes proteolytic processing at a release site (R-site) at its N-terminus and at a maturation site (M-site) near its C-terminus. This proteolysis is mediated by a virally-encoded serine protease (Pr) (Liu and Roizman, 1991; Preston, et al., 1992;

Welch, et al., 1991). Cleavage of AP by the viral Pr is essential for viral growth; HSV mutants bearing an inactive Pr accumulate capsids lacking viral DNA (Desai, et al., 1994; Gao, et al., 1994; Preston, et al., 1994; Preston, et al., 1983; Sherman and Bachenheimer, 1988; Thomsen, et al., 1994). Presumably, cleavage of AP is required to allow its release from the capsid and permit the packaging of newly replicated viral DNA.

This section describes nucleic acid and protein sequences of a novel protease and associated assembly protein that have now been isolated from Kaposi's Sarcoma Herpes Virus (KSHV) and which form the basis for the present invention. These compositions are useful in a number of applications, including screening assays for viral protease inhibitors useful in the treatment of Kaposi's Sarcoma, as described in Section III, below.

1. KSHV Protease Coding Sequences

FIG. 1 shows a schematic diagram of a partial genome of KSHV and the location of ORF 17, indicating the positions of the assembly protein and the KSHV protease that is the subject of the present invention. DNA fragments were isolated from a clone of KSHV previously isolated (Gao, et al., 1994) and known to encode a thymidine kinase molecule. The fragments were sequenced to provide the coding regions for the KSHV protease and assembly protein as detailed in Example 1. In studies carried out in support of the present invention, the 1.5 kb and 0.8 kb fragments were found to contain DNA sequences that encoded a protein that, when aligned with a protease isolated from herpesvirus saimiri (HVS), reveals a sequence identity that is less than 60%, as discussed below.

FIGS. 2A–2B show the coding sequence, identified as SEQ ID NO:1, which encodes the polyprotein comprising the KSHV protease (Pr; nt 1-nt 690) and assembly protein (AP; nt 691-nt 1591). Inspection of the deduced amino acid sequence reveals that the protease sequence is unique, having only a 56% sequence identity with the closest herpes virus protease, herpesvirus saimiri (HVS).

FIGS. 2C and 2D show two alternative 3' extensions of the nucleotide sequence of SEQ ID NO:1, the extensions which are identified herein as SEQ ID NO:2 and SEQ ID NO:3. Addition of the nucleic acid sequence SEQ ID NO:2 to the 3' end of SEQ ID NO:1 results in the sequence identified herein as SEQ ID NO:4, while addition of SEQ ID NO:3 to the 3' end of SEQ ID NO:1 results in SEQ ID NO:5. These 3' extensions correspond to the extreme C-terminal portion of the assembly protein and comprise part of the C-terminal fragment which is proteolytically cleaved away from mature AP by the Pr protease as described below.

The present invention includes the above-described coding sequences for KSHV protease and assembly protein, in combination (SEQ ID NO:1, SEQ ID NO:4 or SEQ ID NO:5) or as separate coding regions for Pr (SEQ ID NO:6) and for AP (SEQ ID NO:8 or SEQ ID NO:9). Also forming part of the present invention are nucleotide sequences that contain alternate codons effective to encode a protein having the sequence identified as SEQ ID NO:7, SEQ ID NO: 10, or SEQ ID NO:11. Such alternate codons may be selected based on codon preferences characteristic of a particular cell type in which the encoded proteins are to be expressed, or may be selected based on known codon equivalencies, according to methods well known in the art.

As discussed in Part B, below, the invention also includes KSHV Pr and AP amino acid sequences that exhibit substantial sequence identity to those presented herein as SEQ ID NO:7, SEQ ID NO:10, and SEQ ID NO:11; accordingly, the invention further includes nucleotide coding sequences that encode such substantially identical protein sequences. Design and construction of such nucleotides will be apparent to those skilled in the art, in view of the present teachings.

The foregoing coding sequences have a number of utilities. One exemplary utility is in the production of the encoded KSHV protease and/or AP. For example, the coding region is inserted into vectors used to transform competent cells for expression of the protein(s). Such recombinant proteins are then used, for example, as reagents in the tests described herein.

Further comprising a part of the present invention are vectors that contain the above-described nucleotide coding regions. Selection of particular vectors for use with specific cell types will be within the skill of persons skilled in the art of recombinant protein expression.

The invention further includes polynucleotide probes that specifically hybridize with SEQ ID NO:1, SEQ ID NO:4, or SEQ ID NO:5. Design parameters of such probes will depend on their particular application; such probes are particularly useful, for example, in test kits, particularly in test kits designed to detect expression of the foregoing Pr or AP proteins.

Coding sequences of the present invention are also used in the design and manufacture of anti-sense-based therapeutics, according to methods known in the art. Such anti-sense compositions may be produced as phosphorothioate oligodeoxynucleotides of about 15–40 bases in length, according to standard methods known in the art. Crude reaction mixture is purified, for example, using NENSORB chromatography (DuPont). Drug delivery methods and pharmaceutical compositions can also be used for anti-sense compositions, according to methods well known in the art.

2. KSHV Protease a. Isolation of KSHV Protease

FIG. 3A shows the deduced amino acid sequence of KSHV Pr, as identified in studies carried out in support of the present invention. KSHV Pr is a 230 amino acid polypeptide when released from the Pr-AP precursor.

Also shown in FIG. 3A are regions indicated as CD5, CD2, CD4, CD3, CD1, CD6, CD7, and R-site, in accordance with standard herpesvirus terminology. The "CD" regions correspond to seven highly conserved domains (CDs) previously identified in other herpesvirus proteases (Loutsch, et al., 1994). In the KSHV protease identified herein as SEQ ID NO:7, areas corresponding to these domains span Leu5 to Ser15 (CD5), Leu40 to Thr55 (CD2), Gly64 to Ser73 (CD4), Trp109 to His119 (CD3), Val131 to Tyr150 (CD1), Phe161 to Val164 (CD6) and Leu196 to Ile222 (CD7).

A further discovery of the present invention is that the KSHV protease contains a putative "catalytic triad" that consists of Ser114, His46 and His134.

The release site (R-site) represents the sequence between KSHV Pr and AP. This site was identified by the presence of an Ala/Ser dipeptide, which is characteristic of other herpesvirus R-sites. The R-site sequence is Tyr-Leu-Lys-Ala*Ser-Gln-Phe-Pro in KSHV (where the asterisk (*) represents the scissile bond), and is identified herein as SEQ ID NO: 12. This region has the characteristic P1 and P1' positions of herpesvirus proteases, but vary in the flanking positions when compared to the other members of the herpesvirus family.

The amino acid sequence of the release site of KSHV protease (Tyr-Leu-Lys-Ala*Ser-Gln-Phe-Pro; FIG. 3A and SEQ ID NO:12) and the AP maturation site (Arg-Leu-Glu-Ala*Ser-Ser-Arg-Ser; FIG. 3B and SEQ ID NO:13) suggest that the extended substrate binding pocket differs from that of other members of the herpesvirus family.

The oxyanion stabilization signature sequence containing Gly-Arg-Arg-X-Gly-Thr was identified at residues 141 to 146; this sequence is also characteristic of herpesvirus proteases.

In accord with the present discovery of the amino acid sequence of KSHV Pr, the invention further includes amino acid sequences that exhibit substantial sequence identity with SEQ ID NO:7, including conservative substitutions thereof. In this context, an amino acid sequence will be considered to be substantially identical to SEQ ID NO:7, if it exhibits at least 70%, preferably 80%, and more preferably 90% sequence identity to SEQ ID NO:7. As mentioned above, the closest known sequence exhibits only a 56% sequence identity with KSHV Pr.

With the knowledge of the KSHV Pr amino acid sequence described above, persons skilled in the art will be able to design and construct proteins having the requisite sequence identity and/or exhibiting conservative amino acid substitutions into regions not specifically identified as essential. Essential amino acid positions are identified in the sequence illustrated in FIG. 3A in bold text: His-46 in the CD2 region, Ser-114 in the CD3 region, and His-134, Arg-142, and Arg-143 in CD1. In a preferred embodiment, the essential positions defined above are constant. In other embodiments, the CD regions generally retain the primary sequences as shown in FIG. 3A.

Substitutions at non-essential positions (e.g., all but His46, Ser-114, His-134, Arg-142 and Arg-143) may be made by making amino acid substitutions, preferably conservative amino acid substitutions, to the Pr sequence. Standard substitution classes that can be used in this analysis are the six classes based on common side chain properties and highest frequency of substitution in homologous proteins in nature, as determined, for example, by a standard Dayhoff frequency exchange matrix (Dayhoff, 1972). These classes are Class I: C; Class II: S, T, P, A, and G (representing small aliphatic side chains and OH-group side chains); Class III: N, Q, D, and E (representing neutral and negatively charged side chains capable of forming hydrogen bonds); Class IV: H, R, and K (representing basic polar side chains); Class V: I, V, L (representing branched aliphatic side chains) and M; and Class VI: F, Y, and W (representing aromatic side chains). In addition, each group may include related amino acid analogs, such as ornithine, homoarginine, N-methyl lysine, dimethyl lysine, or trimethyl lysine in class IV, and cyclohexylalanine or a halogenated tyrosine in Group VI. Further, the classes may include both L and D stereoisomers, although L-amino acids are preferred for substitutions.

Polypeptide sequences designed according to the foregoing guidelines can be produced, for example by recombinant expression. Modifications in the coding sequence may be made by standard well-known mutagenic techniques. Alternatively, recombinant expression can be effected by synthesizing segments of desired oligonucleotides corresponding to native KSHV or substitution variant of KSHV Pr as described above. Such oligonucleotides can then be spliced together to form a polynucleotide which is insertable into a vector for recombinant expression.

3. KSHV Assembly Protein

According to a related discovery of the present invention, the DNA sequence of SEQ ID NO:8 predicts a novel assembly protein (AP) that exhibits less than 50% sequence identity to an assembly protein identified in HVS. The predicted M-site cleavage site is composed of Arg-Leu-Glu-Ala*Ser-Ser-Arg-Ser (FIG. 3B; SEQ ID NO:13). In general, M-site residues of herpesvirus assembly proteins show more variety than R-site sequences; except for P1 and P1', none of the other residues of the site is conserved. Cleavage of AP at the M-site by Pr releases the 283 amino acid mature AP from the carboxy-terminal fragment.

The present invention therefore includes the AP amino acid sequence identified as SEQ ID NO:10, as illustrated in FIG. 3B, as well as polypeptide sequences that have substantially identical sequences; e.g., greater than or equal to about 70% sequence identity. The invention further includes alternative C-terminal peptide extensions of the sequence SEQ ID NO:10, the preferred embodiment of which is identified herein as SEQ ID NO:11. The C-terminal extension (labeled EXT in FIG. 3B) extends the peptide fragment which is cleaved from the mature AP protein. Conservative substitutions may be made within any of these sequences, for example, according to the paradigms described in Part B, above.

4. Structure of KSHV Pr

In view of experiments and observations carried out in support of the present invention, it is likely that the KSHV Pr is active when it forms a homodimer composed, for example, of two molecules of the polypeptide described herein as SEQ ID NO:7. A dimer interface region is identified in the KSHV protease at positions 192–205 of SEQ ID NO:7 (PLETLMAKAIDASF; identified herein as SEQ ID NO:14). The existence of the protease in dimer form provides opportunities to develop specific inhibitors of its enzymatic activity, as discussed in Section III.B., below.

5. Production of KSHV Protease and Assembly Proteins a. Recombinant Expression KSHV Pr and AP may be produced recombinantly by any of a number of methods available for expression of proteins. Expression of the KSHV Pr and AP and proteins having substantial sequence identity thereto can be carried out in any of a number of cellular expression systems. Possible host cells include, but are not restricted to, bacterial, yeast, insect, and mammalian cells. Example 2 provides methods for expression of KSHV protease in bacteria, yeast and insect cells.

The present invention includes recombinant constructs comprising one or more of the nucleotide sequences as broadly described above. The constructs comprise a vector, such as a plasmid or viral vector, into which a sequence of the invention has been inserted. In a preferred aspect of this embodiment, the construct further comprises regulatory sequences, including, for example, a promoter, operably linked to the sequence. Large numbers of suitable vectors and promoters are known to those of skill in the art, and are commercially available. Appropriate cloning and expression vectors for use with prokaryotic and eukaryotic hosts are also described in, e.g., Ausubel, et al., (1990).

The present invention also relates to host cells which are genetically engineered with vectors of the invention, and the production of polypeptides of the invention by recombinant techniques. Host cells are genetically engineered (i.e., transduced, transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the Pr or AP genes. The culture conditions, such as temperature, Ph and the like, are those previously used with the host cell selected for expression, and will be apparent to those skilled in the art.

Proteins can be expressed intracellularly or extracellularly. For bacterial expression, the proteins can be expressed as inclusion bodies or in soluble form. It is appreciated that expression in a particular system may be optimized by tailoring codons to the particular cell type in which expression is to occur. Hence polynucleotides encompassed by the present invention shall include polynucleotides coding for the protein of interest, as modified for optimal expression in any given expression system, without regard to the overall sequence identity to SEQ ID NO:1, SEQ ID NO:4, or SEQ ID NO:5 (Pr/AP coding sequences), SEQ ID NO:6 (Pr coding sequence), SEQ ID NO:8 or SEQ ID NO:9 (AP coding sequences). Such designing can be effected with the aid of codon usage or preference tables such as are known in the art.

In studies carried out in support of the present invention, the portion of the KSHV ORF corresponding to the viral Pr was subcloned into an *E. coli* expression vector transcriptionally regulated by an IPTG-inducible promoter (Example 3). An amino-terminal His$_6$ tag was incorporated into the Pr ORF to facilitate purification. A variant was also constructed in which the active-site Ser-114 was converted to Ala (Variant S114A). Following overexpression of His$_6$-Pr and His$_6$-Pr(S114A), these proteins were subjected to metal-chelate affinity chromatography under denaturing conditions, eluted, and refolded. Purified protein, as well as samples from throughout expression and purification, was analyzed by SDS-PAGE and deemed greater than 90% pure. A protein yield of roughly 10 mg from one liter bacterial cultures was obtained.

Expression of KSHV Pr and the S114A variant in *E. coli* yielded bands which migrated near 31 kD on SDS-PAGE, corresponding to the full-length translated Pr domain, terminating at the putative R-site alanine residue. This apparent size, slightly larger than the expected 27 kD, is most likely due to incorporation of the His$_6$ tag. Two faster-migrating proteolytic fragments were also observed that may have resulted from autoproteolysis. The S114A variant was observed to be significantly more homogenous when analyzed by SDS-PAGE, possibly due to lower levels of autoproteolysis. In order to verify that the extra bands are not contaminating *E. coli* polypeptides, the products were examined by immunoblotting with an antibody raised to the recombinant, full-length Pr. A control bacterial extract was analyzed on the same inmmunoblot as the purified His$_6$-Pr material, and gave rise to no significant, specific immunore-activity of the same bands in the purified fraction of His$_6$-Pr. These results indicate the purity of the protein fractions and the specificity of the polyclonal antibody, α-KSP, for KSHV Pr. As a further control, a parallel immunoblot was assayed with a commercially available monoclonal antibody (Qiagen, Chatsworth, Calif.) directed against the amino-terminal Arg-Gly-Ser-His$_4$ epitope of His$_6$-Pr. This experiment yielded essentially the same set of bands as did the polyclonal antibody α-KSP. The additional protein species thus contain the amino-terminal His$_6$-tag, and have arisen due to proteolysis during expression and/or purification by either an endogenous bacterial enzyme, or to autodigestion of KSHV His$_6$-Pr at sites other than the R-site Ala*Ser.

In further studies performed in support of the present invention, Pr and the variant S204G were expressed in an *E. coli* expression system without the amino-terminal His$_6$-tag. The Pr(S204G) variant was engineered to stabilize the enzyme against autoproteolysis and had essentially the same activity as Pr when assayed according to the method of Example 5.

b. In vivo Transcription of KSHV AP and Pr/AP mRNAs

The KSHV-infected B-cell line, BCBL-1, was employed for transcription of the KSHV Pr/AP and AP genes during lytic infection. This cell line harbors the viral genome in latent form, and treatment of these cells with TPA induces lytic replication (Renne, et al., 1996). Equivalent amounts of poly(A)-enriched RNA from uninduced or induced BCBL-1 cells in the presence or absence of phosphoroformic acid (PFA), an inhibitor of herpesviral DNA replication, were separated on a formaldehyde/agarose gel, transferred to a membrane, and hybridized to a probe derived from the 1.5 kb fragment containing the Pr/AP ORF of KSHV, as detailed in Example 6.

Examination of the Northern blot revealed, in the lane containing RNA from uninduced cells, a faint band migrating at approximately 0.95 kb, which is the expected size of the AP transcript. This 0.95 kb band was absent in the lane which contained RNA from uninduced, PFA-treated cells, indicating that production of the transcript was strongly inhibited by the herpesviral DNA replication inhibitor. Production of the 0.95 kb AP transcript was strongly upregulated in the BCLB-1 cells upon lytic induction of KSHV by TPA treatment; an additional transcript migrating at approximately 2.3 kb was also observed. The size of the additional transcript is consistent with what would be expected from the transcript encoding the Pr/AP ORF. Production of both the 0.95 kb and 2.3 kb transcripts was strongly inhibited in the presence of PFA in the TPA-induced cells, indicating that they are late transcripts.

6. Catalytic Activity of KSHV Pr

According to an important aspect of the invention, the KSHV proteases defined by the present invention exhibit catalytic activity that is within the range of catalytic activities defined by recombinant KSHV Pr (SEQ ID NO:7), as isolated. In this context, "within the range" means that the protein has catalytic activity that is at least $\frac{1}{10}$ that of KSHV Pr and preferably at least $\frac{1}{5}$ that of KSHV Pr. Proteins having higher catalytic activities are acceptable, as well.

Such activities can be determined by comparing the activity of a KSHV PR, as defined herein, to that of the KSHV Pr having the sequence SEQ ID NO:7. For example, in experiments carried out in support of the present invention, recombinantly produced His$_6$-KSHV Pr and variant His$_6$-KSHV Pr(S114A) proteins were tested for ability to cleave a synthetic peptide substrate. The substrate, containing the HCMV M-site peptide sequence RGVVNASSRLA (SEQ ID NO:15) flanked by a fluorogenic donor-acceptor pair, allows for continuous monitoring of peptide hydrolysis due to fluorescence enhancement arising from donor-acceptor separation (Holskin, et al., 1995). This substrate contains an internal Arg residue, allowing for cleavage by trypsin, an extremely well-characterized serine protease.

Figure 4A:
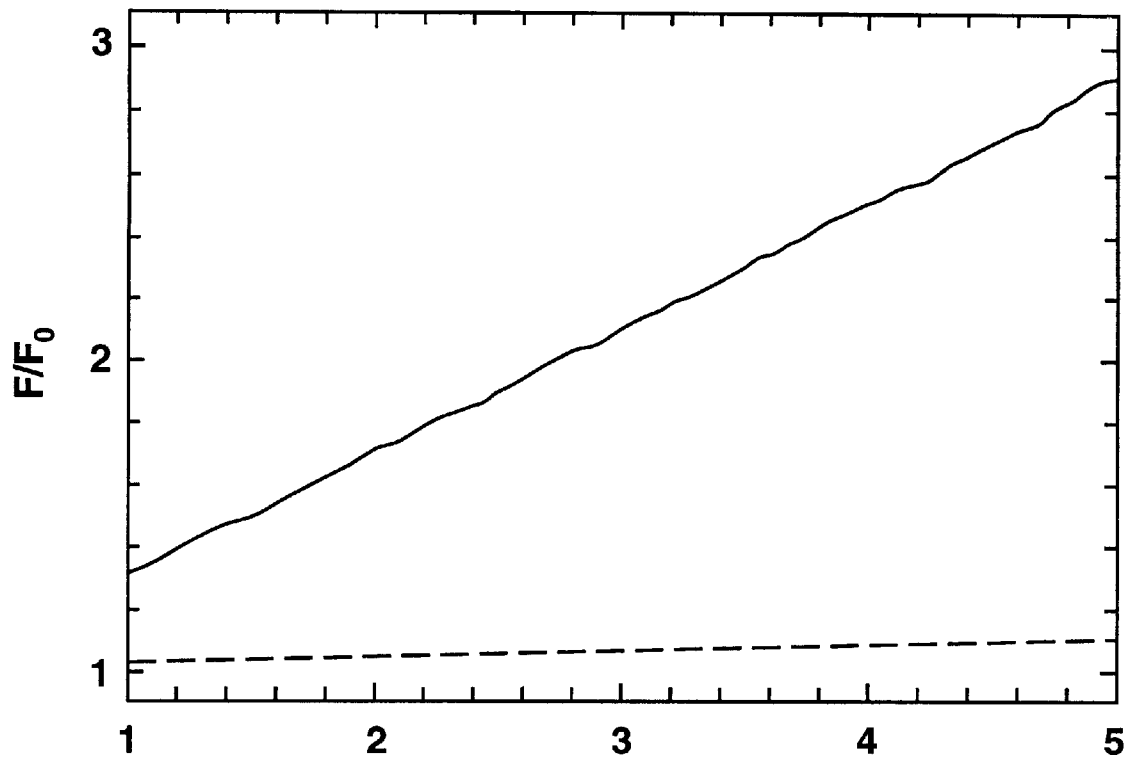
FIGS. 4A and 4B show plots of a continuous fluorometric assay of KSHV His$_6$-Pr, KSHV His$_6$-Pr(S114A), trypsin, and trypsin D102N, where time-evolved fluorescence (F) normalized to initial fluorescence output ($F_o$), is plotted versus time (hours), in a 5-hour time course of steady-state peptide hydrolysis by purified 1.5 μM KSHV His$_6$-Pr (solid line) and of 1.5 μM KSHV His$_6$-Pr(S114A), (dashed line) (4A), and a one-hour time course monitoring the kinetics of 1 Nm trypsin (dashed line), 1.0 μM trypsin D102N (broken line), 1.5 μM KSHV His$_6$ Pr (solid line), and 1.5 μM KSHV His$_6$ Pr(S114A) (dotted line) (4B), where the inset shows plots of activity of KSHV His$_6$ Pr (solid line), and 1.5 μM KSHV His$_6$ Pr(S114A) on a finer scale (dotted line)

As shown in FIG. 4A, there is a significant difference in apparent proteolysis catalyzed by 1.5 μM KSHV Pr and the active-site variant S114A. While there is a slight fluorescence enhancement induced by the S114A variant (dotted lines) over the one and five hour time courses of the separate experimental data sets, this increase is negligible compared to the marked increase in this activity exhibited by the native enzyme (solid line). By five hours there is a nearly three-fold increase in fluorescence intensity for the KSHV Pr-catalyzed reaction, while the S114A variant exhibits minimal enhancement, perhaps due to some residual proteolytic activity. Thus, there is specific cleavage of a related herpesvirus maturation site, catalyzed by the purified, His$_6$-tagged KSHV Pr molecule.

Figure 4B:
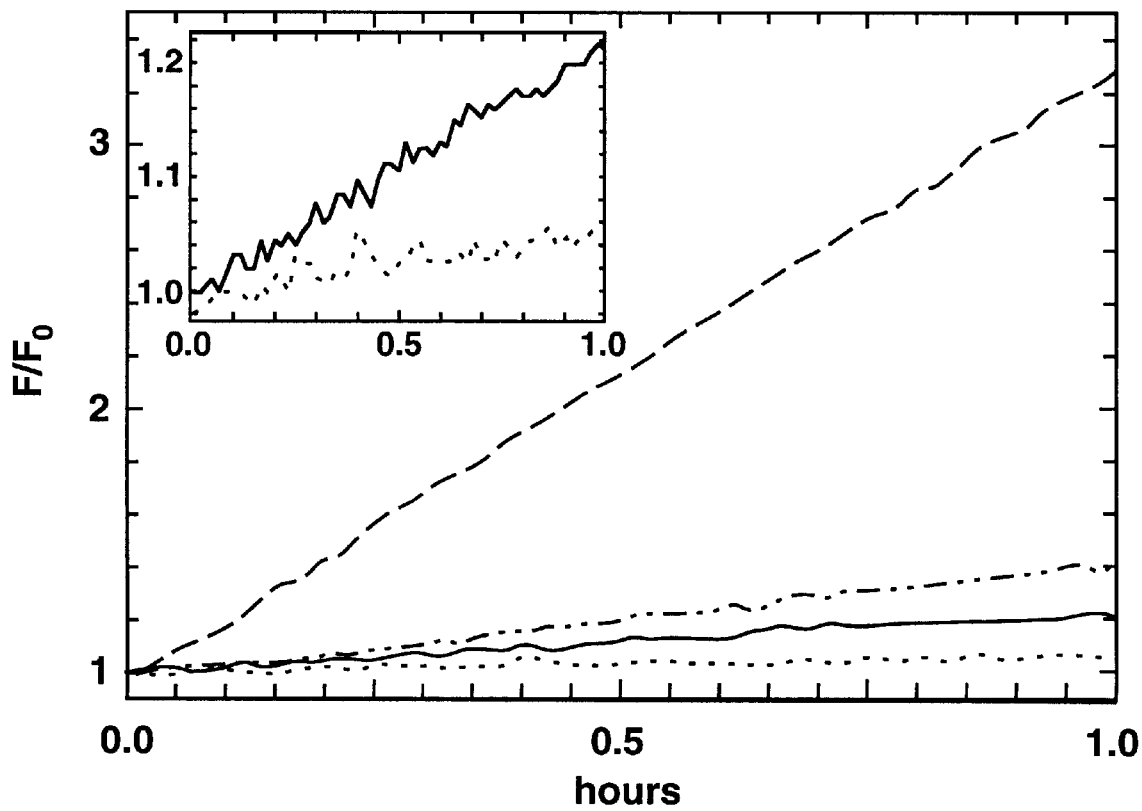

The proteolytic activity of the newly identified KSHV protease KSHV Pr was also compared with that of trypsin and trypsin D102N, using a standard protease assay (Craik, et al., 1987). Trypsin has an extremely high rate of catalytic turnover, and has served as a model for site-specific enzyme-directed peptide hydrolysis. Trypsin D102N, in which the active site Asp residue has been replaced with Asn, has a catalytic efficiency that is orders of magnitude lower than trypsin, depending on solution conditions (roughly 5000-fold lower under the conditions used herein). 1 nM trypsin hydrolyses the HCMV substrate at a much higher rate than 1.5 μM KSHV Pr, indicating that trypsin is substantially more active than the KSHV enzyme (FIG. 4B, dashed and solid lines, respectively). On the other hand, 1 μM trypsin D102N catalyzes this reaction only 2-fold faster than a comparable concentration, 1.5 μM, of wild-type KSHV Pr (FIG. 4B, broken and solid lines, respectively). Thus, the lack of an active site Asp, with conservation of the other two catalytic triad members, His and Ser, results in similar rates of peptide hydrolysis by two unrelated serine proteases, whether engineered as in trypsin, or naturally occurring as in KSHV Pr.

The foregoing assay serves as a test to ensure that substitution variant protease proteins formed as described in Section B, above, are active and therefore useful in further practice of the invention. For example, in the examples provided above, while the S114A variant of KSHV Pr exhibits sufficient sequence identity to the native KSHV Pr (SEQ ID NO:7) to be considered within the family of KSHV proteases defined herein, it lacks an essential amino acid (serine) residue at position 114, and it lacks the critical activity in a proteolytic assay (e.g., its activity is not at least ¹⁄₁₀ that of KSHV Pr having the sequence SEQ ID NO:7). Therefore, KSHV Pr(S114A) would not be considered an active KSHV protease within the invention described herein.

III. KSHV Protease Inhibitors

It is appreciated that inhibitors of KSHV protease are useful therapeutics for inhibiting and/or preventing infection by KSHV. The present invention provides methods for designing such inhibitors, based, for example, on (i) non-hydrolyzable peptide analogs, such as M-site or R-site analogs, and (ii) formation of inactive KSHV Pr dimers. Examples of how such inhibitors are designed and/or identified and tested are provided in the following sections.

1. Non-Hydrolyzable Cleavage-Site Peptide Analogs

According to an important feature of the invention, an HCMV M-site peptide substrate having the sequence RGV-VNASSRLA (SEQ ID NO:15) has been determined to be a cleavable substrate of the KSHV protease. As described in Example 5, this substrate is cleaved between its alanine and serine residues. Non-hydrolyzable analogs can be formed based on this substrate, and based on other peptide substrates identified using the methods described herein, by modifying the peptide by one or more of methods known in the art. For example, D-amino acids may be substituted for L-amino acids in the substrate. Other approaches to preparing non-hydrolyzable analogs include, but are not limited to, the use of alkyl backbone moieties joined by thioethers or sulfonyl groups, alkyl backbone moieties joined by carbamate groups, and peptoid backbones.

Additionally, the KSHV protease exhibits proteolytic activity at the AP M-site located near the C-terminal portion of AP, having the sequence RLEASSRS (SEQ ID NO:13). The KSHV protease also exhibits proteolytic activity at the R-site, having the sequence YLKASQFP (SEQ ID NO:12), which is the junction between Pr and AP in the precursor polyprotein. Accordingly, peptides derived from these regions, and particularly, transition state analogs of such peptides and analogs designed to fill the P1-P1' pocket formed by the above-mentioned catalytic triad in Pr, along with the above-identified substrate, form the basis for peptide inhibitors of KSHV protease. Design of space-filling analogs is now feasible using a combination of computer programs such as DOCK for analyzing the 3-dimensional structure of the protease and for creating peptides designed to fill specific sites (DesJarlais, et al., 1990).

Figure 5A:
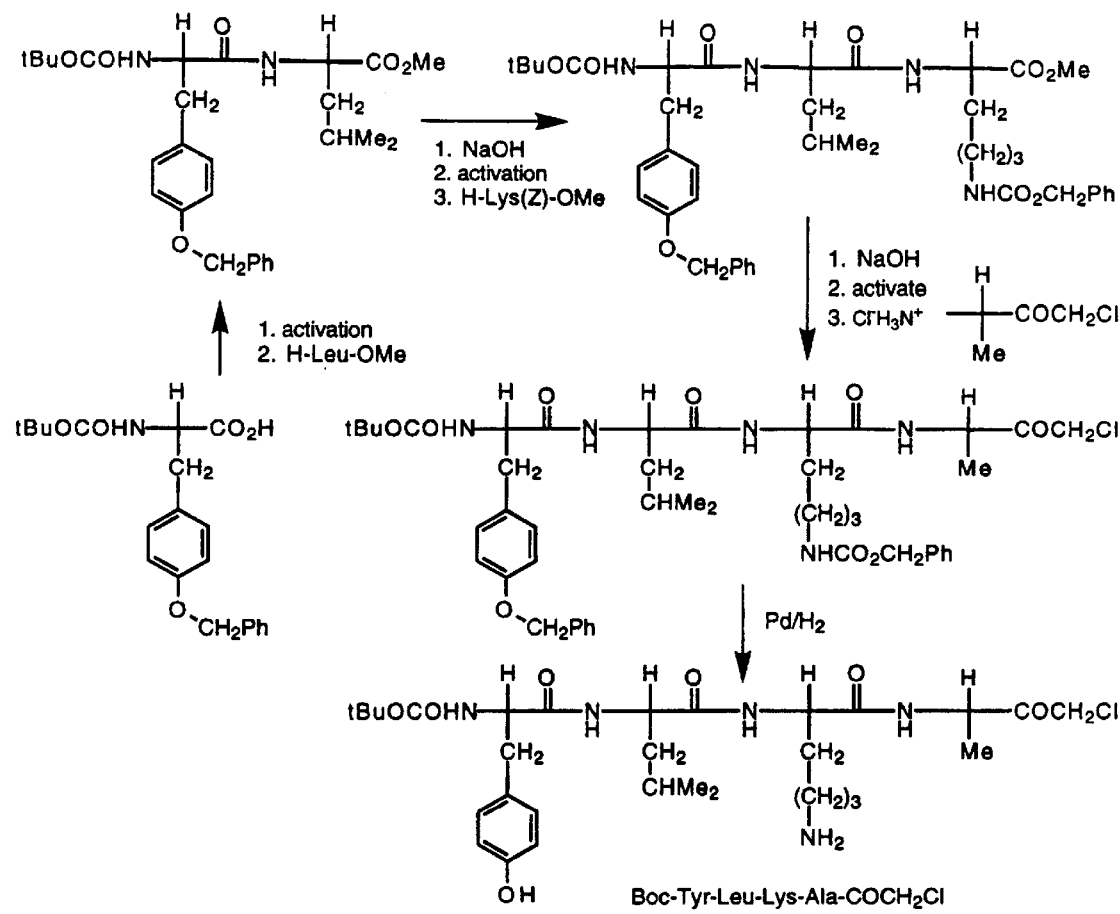
FIGS. 5A and 5B show reaction schemes for the synthesis of an irreversible KSHV protease inhibitor (5A) and of the chloromethyl ketone derivative of a Boc-protected alanine (5B)
Figure 5B:
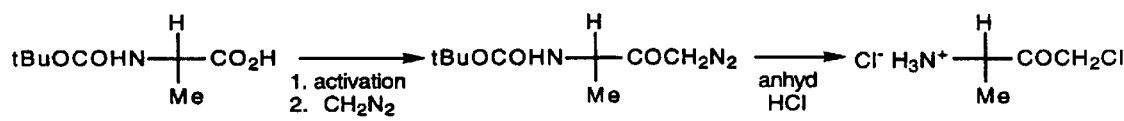

An exemplary irreversible peptide inhibitor based on the KSHV R-site sequence and having a choloromethylketone at the C-terminus is Boc-YLKA-COCH$_2$Cl (where Boc- is t-butyloxycarbonyl). A bromomethylketone (COCH$_2$Br) may be used as well. Synthesis of this compound is achieved by the steps shown in FIGS. 5A and 5B. Briefly, a Boc- and benzyl-protected tyrosine, activated by reaction with isobutyl chloroformate/N-methylmorpholine is condensed with a methyl esterified leucine residue to give a protected dipeptide. Hydrolysis of the methyl ester provides the free carboxylic acid group required for introduction of an alanine modified to incorporate the choloromethylketone function. To make the modified alanine, Boc-protected alanine is reacted with isobutyl chloroformate/N-methyl morpholine in THF at −20° C. (Kettner, et al., 1981). Reaction of diazomethane with the resulting anhydride followed by treatment with anhydrous HCl leads to precipitation of the hydrochloride salt of the desired 3-amino-1-chloro-2-butanone. Condensation of this amine with the activated, protected tripeptide produces the protected peptide which, after deprotection by catalytic hydrogenation over Pd should yield the desired peptide. The α-bromomethylketone analogue is synthesized either by a similar procedure or by nucleophilic displacement of the chloride by a bromide.

An aldehyde analogue of the chloromethylketone function can be introduced into the peptide to provide enhanced inhibitory activity, e.g., Boc-YLKA-COCHO. The synthesis of this compound is as described above, except that the protected alanine aldehyde is substituted for the chloromethylketone in the last step of the sequence. Likewise, a boronic acid function can be added, according to methods known in the art, and is particularly useful where the catalytic serine residue of the KSHV protease exhibits relatively low reactivity, e.g., lower activity than that of conventional serine proteases.

Other peptide sequences useful as substrates or as forming the basis for inhibitors are identified through screening of combinatorial libraries, such as a heterocyclic or peptoid library, such as is available from ArQule, Inc. (Medford, Mass.). Such libraries can be efficiently screened according to methods known in the art.

Ideally, such peptide inhibitors are small molecules that are orally available; alternatively, the peptide inhibitors may be formulated for intravenous injection. The peptides can be further designed for enhanced stability in vivo, for example, by substituting D-amino acids into the structure or by alternate backbone structures.

A variety of backbone types can be used for ordering and positioning the acid and non-acid moieties of the polymer composition, including, for example, alkyl backbone moieties joined by thioethers or sulfonyl groups, alkyl backbone moieties joined by carbamate groups, and peptoid backbones. Methods for preparing peptides having alternate backbones and for producing peptides having enhanced stability, as well as peptide therapeutic delivery systems, are known in the art (see e.g., Banga, 1995).

2. Dysfunctional KSHV Pr Dimers

It is the discovery of the present invention that the KSHV protease may exist and function as a dimer of two Pr polypeptides, such as two of the polypeptides of SEQ ID NO:7. While not relying on any particular mechanistic theory, it is suggested that optimal catalytic activity in vivo may require dimer formation.

According to this discovery, KSHV protease activity may be effectively inhibited by association of inactive Pr monomers with active monomers to form a dysfunctional Pr dimer. Dysfunctional dimers may be also formed by addition of a monomer fragment that includes the dimer interface region, e.g., residues 192–205 of the KSHV protease sequence (SEQ ID NO:14). Other forms of inactive monomers include fragments of the protease monomer that block formation of the dimer. Thus, truncated monomers or peptides that mimic the binding site interface can be used to block dimerization. In this context, it is anticipated that the interaction between the inactive monomer or peptide will inhibit the active monomer by an allosteric interaction at the interaction site.

Polynucleotide sequences encoding inactive monomers can be readily designed and manufactured using various recombinant DNA techniques well known to those skilled in the art. Polynucleotide sequences encoding inactive monomers can be obtained from a number of sources. For example, polynucleotides which encode the KSHV Pr described herein (e.g., SEQ ID NO:1 or SEQ ID NO:6) can be modified by any of several well-known techniques, such as oligonucleotide or PCR-mediated site-directed mutagenesis (Ausubel, et al., 1990). Lack of activity of the modified product is verified in a protease activity assay, as described in Example 5.

Suitably small peptides may be used directly as therapeutic agents, by mixing them in a suitable pharmaceutical excipient and administering the therapeutic mixture to a subject, according to clinically acceptable methods known in the art.

Polynucleotides encoding an inactive protein or protein fragment may also be introduced to a subject or cell line by gene therapeutic methods. Any method for delivering the vector containing the inactive protein coding region can be used. In the case of in vivo gene therapy, retroviral and adenoviral vectors have been used to transduce cells. The design of such vectors is well known to persons skilled in the art. Generally, gene therapy techniques may be used to introduce such vectors ex vivo into the cells of a host subject. Alternatively, retroviral particles containing the inactive protease monomers may also be delivered in vivo by systemic administration, e.g., intravenous, intraperitoneal, subcutaneous injection, according to methods known in the art.

Inactive monomers may also be prepared as formulations in pharmaceutically acceptable media, such as saline, phosphate buffered saline, glucose, at a therapeutically effective dose that can be estimated based on measured viral titer in the patient. For purposes of increasing serum half-life or for cellular targeting, monomers may be encapsulated, such as in liposomes bearing targeting moieties that interact with specific cell receptors, according to methods known in the art. Further details of the various ways in which inactive monomers can be used as therapeutics can be found in PCT Publication WO 96/14863.

3. Characterization of KSHV Protease Inhibitors

Figure 6:
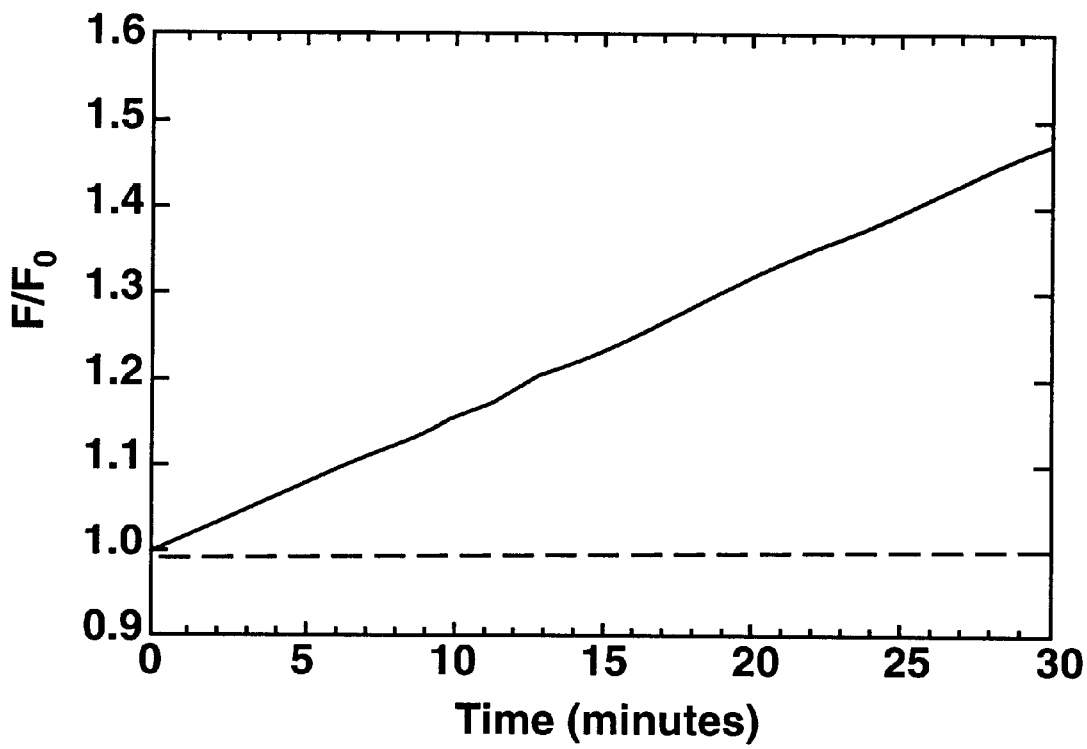
FIG. 6 compares the activity of Pr(S204G), an autolytically stable PR variant, in the absence (solid line) and in the presence (dashed line) of the inhibitor Boc-YLKA-COCH$_2$Cl.

The efficacy of small molecule inhibitors described above is tested in vitro, according to the screening method of the invention. Candidate compounds as described above may be first tested in a protease assay, such as the fluorometric assay detailed in Example 5. FIG. 6 shows the results of such an assay, which compares the activity of Pr(S204G), an autolytically stable variant having substantially the same activity as Pr, in the absence and in the presence of the exemplary Boc-YLKA-COCH$_2$Cl inhibitor described above. Complete inhibition of protease activity was observed following incubation of 0.5 $\mu$M enzyme with 300 $\mu$M inhibitor.

Once candidate inhibitor compounds are identified in this or in a comparable in vitro assay, the candidate inhibitors are then assayed in biological systems, such as in intact cells.

For putative irreversible inhibitors, such as the exemplary chloromethylketone derivative described above, time dependence and irreversibility of the reaction are determined. Subsequent studies are carried out to determine the rate of inactivation ($k_{inact}$), the stoichiometry of the reaction and the specific amino acid modified by the reaction. Labeling of the KSHV protease can be detected by SDS-PAGE, HPLC and electrospray mass spectral analysis of the intact enzyme adduct, according to methods known in the art (see, e.g., Salto, et al., 1994; Yu, et al., 1996).

An exemplary cellular assay for KSHV protease inhibitors involves measuring the processing of the assembly protein precursor by KSHV protease (autoproteolysis). The level of autoproteolytic activity is followed by monitoring the formation of KSHV protease and assembly products according to methods known in the art. In the presence of inhibitor, only the starting material, the precursor protease/AP polyprotein, will be detected. Detection can be achieved by methods known in the art, such as by SDS-PAGE analysis of the reaction products, and/or immunoblot analysis using antibodies directed to the C-terminus of KSHV protease or to the N-terminus of AP.

Figure 7:
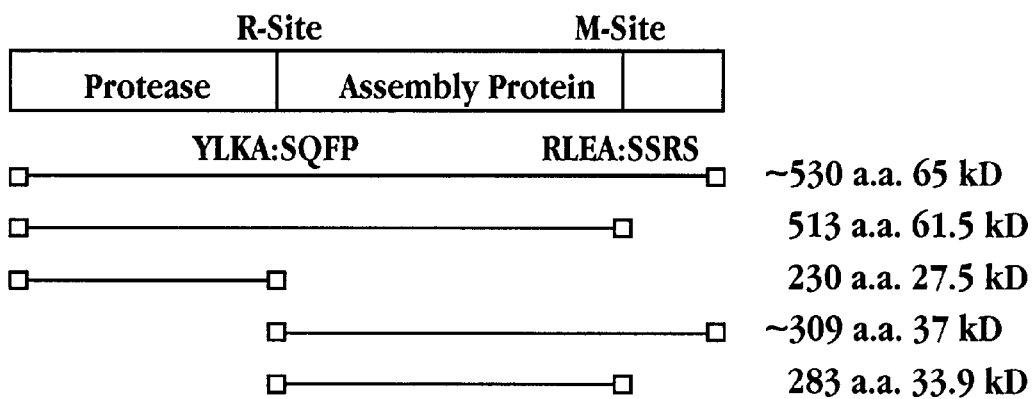
FIG. 7 is a schematic diagram of the KSHV Pr/AP polyprotein precursor, showing the R-site and M-site sequences and the approximate sizes of the products produced by Pr-catalyzed proteolytic cleavage.

Another exemplary cellular assay involves use of the eukaryotic expression vector RSV.5neo (Long, et al., 1991) to express KSHV protease or Pr/Ap precursor in human adenocarcinoma kidney cells (AKC-293 cells, American Type Culture Collection, Manassas, Va.). Expression and activity of the protease is followed by Western blot analysis. The expressed Pr/AP polyprotein precursor is approximately 530 amino acids (approx. 65 kD) and is cleaved by uninhibited KSHV protease to create a 230 amino acid (27.5 kD) protease and a 283 amino acid (34 kD) mature AP, as shown schematically in FIG. 7. The relative intensities of the polyprotein band and the protease band reflect the activity of the protease. When inhibitory compounds are tested in this assay, there should be a relative lack of appearance of protease band detected in the gel, and maintenance of the higher molecular weight Pr/AP precursor polyprotein.

IV. Treatment Methods

The invention includes a method of treating a mammalian subject exhibiting symptoms of Kaposi's sarcoma or harboring the KSHV virus. The treatment method may also be used in a prophylactic protocol to prevent infection by KSHV.

According to the treatment method, an effective amount of one or more of the peptide-based inhibitors or protein monomers described in the foregoing sections is administered to the patient. The effective amount can be estimated, based on the concentration of the particular agent that is effective in an appropriate in vivo or in vitro model, such as in the protease inhibition assays described above. The effective concentration is then extrapolated to a human dosage, according to known principles of biodistribution and pharmacodynamics.

As an example, the peptide inhibitor Boc-YLKA-COCH$_2$Cl is tested at various concentrations in one of the cellular model systems discussed above. An IC50 (concentration at which protease is inhibited by 50%) is determined for this compound in the assay. From these measurements, estimates of the affinity can be made ($K_i$). Additional inhibitors designed according to the methods described above are deemed to fall within the scope of the therapeutic composition, if they are active at doses between about 0.01 and 10 times this $K_i$.

In a related aspect, the invention includes therapeutic compositions and methods of treatment that include, in addition to one or more of the KSHV protease inhibitor compositions described above, an additional anti-viral composition. For example, persons harboring KSHV are often also infected with human deficiency virus (HIV). Therefore, anti-KSHV protease inhibitors may be co-administered with anti-HIV drugs, such as zidovudine (AZT), ribavirin, or HIV protease inhibitors indinavir (Crixivan™), saquinavir (Invirase™), ritonavir (Norvir™), or nelfinavir (Viracept™). KSHV-specific inhibitors may also be combined with other compounds known to be effective against herpesviruses, such as acyclovir, gangiclovir, adenine arabinoside (Ara-A, vidarabine) or foscarnet, or with other general anti-viral agents, such as amantadine, rimantadine, ribavirin interferons, and the like. Effective clinical dosages of these agents are well known in the art. Combination therapy may require more or less of either of the components than would be required alone. Adjustments in dosage can be made as clinically appropriate, aided by the diagnostic methods discussed in Section V, below.

V. Screening and Diagnostic Methods

In another aspect, the invention includes methods for screening new compounds and methods for diagnosing infection by KSHV. Such methods are described in the sections that follow.

1. Screening Assays

The protein and polynucleotide sequences described herein can be used in the context of screening assays designed to identify new compounds that inhibit KSHV protease. Inhibition of KSHV protease can be measured in any of a number of protease assay formats known in the art, including, but not limited to, spectroscopic assays, protein substrate analysis (SDS-PAGE) assays, mass spectroscopic techniques, and the like.

One exemplary spectroscopic fluorometric assay for measuring KSHV protease activity is detailed in Example 5. Here, the fluorogenic peptide substrate DABCYL-Arg-Gly-Val-Val-Asn-Ala-Ser-Ser-Arg-Leu-Ala-EDANS is mixed with isolated KSHV protease in the absence or presence of a test compound, and fluorescent signal is measured that is proportional to the extent of peptide cleavage. A compound is considered an inhibitor of KSHV protease if it substantially reduces the extent of protease-mediated peptide cleavage compared to control. In this context, the term "substantially reduces" means that the difference between protease activity in the presence of the compound and in the absence of the compound is significantly different, as determined by an appropriate statistical test and/or by concentration-effect analysis. Such KSHV inhibitory compounds are useful in treating KSHV infection and Kaposi's Sarcoma.

One or more of the cellular systems discussed in Part C, above, may also be adapted to a screening assay, in accord with the present invention.

The KSHV Pr protein used in such an assay may be a recombinant protein, produced by any of the methods described herein, or by other methods known to practitioners. Preferably, the protein will have at least 70% sequence identity with SEQ ID NO:7 and will exhibit at least 1/10 the proteolytic activity of the KSHV Pr having the sequence identified as SEQ ID NO:7. The protease substrate may be the Pr/AP precursor, or, more conveniently, the fluorogenic peptide mentioned above, or substrate compositions based on any of the peptide substrates described herein (e.g., the M-site peptide of SEQ ID NO:13, the R-site peptide of SEQ ID NO:12).

Test compounds may be selected from any of a number of compound libraries, including expression libraries. In a preferred embodiment, the library is a combinatorial peptide or peptide-based library. As mentioned above, a compound will be considered as an inhibitor of KSHV if it substantially reduces KSHV Pr activity compared to control.

In a further aspect, the invention includes a pharmaceutical preparation of a compound identified as effective as a KSHV protease inhibitor. The practitioner of the screening assay will typically continue to test the efficacy and specificity of the selected compounds both in vitro and in vivo. Whether for subsequent in vivo testing, or for administration to an animal as an approved drug, agents identified in the screening assay can be formulated in pharmaceutical preparations for in vivo administration to an animal, preferably a human.

The compounds selected in the screening assay, or a pharmaceutically acceptable salt thereof, may accordingly be formulated for administration with a suitable pharmaceutical carrier, such as water, buffered saline, polyol (for example, glycerol, propylene glycol, liquid polyethylene glycol and the like) or suitable mixtures thereof, formulated specifically according to the type of substance and preferred mode of administration, according to methods well known in the art. Further, the optimum concentration of the active ingredient(s) in the chosen medium can be determined empirically, according to procedures well known to medicinal chemists. As used herein, "suitable pharmaceutical carrier" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the compound, its use in the pharmaceutical preparation of the invention is contemplated.

Suitable carriers and their formulation inclusive of other proteins are described, for example, in Gennaro, 1990. These carriers include injectable "deposit formulations". Based on the above, such pharmaceutical formulations include, although not exclusively, solutions or freeze-dried powders of the compound in association with one or more pharmaceutically acceptable carriers or diluents, and contained in buffered media at a suitable pH and isosmotic with physiological fluids. In a preferred embodiment, the compound can be disposed in a sterile preparation for topical and/or systemic administration. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions in isotonic solutions of the desired volume and include, but not exclusively, the use of buffered saline solutions with phosphate or citrate at suitable concentrations so as to obtain at all times isotonic pharmaceutical preparations of the desired pH (for example, neutral pH).

2. Diagnostic Assays

The invention also includes, in another aspect, a method of detecting the presence of KSHV in a tissue sample. Here, nucleotide probes are derived from one or more of the polynucleotides described herein, e.g., SEQ ID NO:1, SEQ ID NO:2, SEQ ID NO:3, SEQ ID NO:4, SEQ ID NO:5, SEQ ID NO:6, SEQ ID NO:8 or SEQ ID NO:9, and are designed to be complementary either to the said polynucleotides or, preferably, their deduced RNA transcripts. Preferably, such probes are branched DNA (bDNA) probes which can be used in a signal amplification assay to detect as few as 500–1000 KSHV RNA molecules per milliliter of blood plasma. Preferably, the nucleotide from which the bDNA is derived is the AP coding sequence (SEQ ID NO:8 or SEQ ID NO:9), since levels of AP RNA are expected to be relatively high during certain phases of KSHV infection. Methods for designing and manufacturing such probes are well known in the art.

The probes are contacted with blood plasma sample derived from a patient suspected of harboring KSHV. The sample may be a tissue section suitable for in situ hybridization, or it may be an extract separated on a gel for Northern blot analysis. Design of suitable nucleotide probes, as well as methods of labeling such probes, are well known in the art. Such detection methods may be augmented by addition of polymerase chain reaction (PCR) techniques to the protocols, according to methods known in the art.

In addition, the efficacy of a particular protease inhibitor compound can be assessed in a patient being treated with the compound, using a modification of one or more of the detection methods described above. This assay exploits the discovery of the present invention, that KSHV Pr and AP are initially fused and are released during maturation only upon cleavage by KSHV Pr. Thus, when the protease inhibitor treatment method is effective, Pr/AP will remain in a fused state. To detect the differential status, antibodies directed to the fused portion of the protein, e.g., the intact R-site or the M-site region, can be produced. Such antibodies detect the result of Pr inhibition—lack of maturation of the Pr/AP protein. In addition, antibodies directed to the C-terminus of Pr or the N-terminus of AP can be made. This second type of antibody detects maturation of virus. Tissue samples are probed with both kinds of antibodies to determine the ratio of mature to inmmature viral particles.

While the invention has been described with reference to specific methods and embodiments, it will be appreciated that various modifications and changes may be made without departing from the invention.

The following examples illustrate, but in no way are intended to limit the present invention.

EXAMPLE 1

Isolation of Coding Sequence for KSHV Protease

A partial KS genome had been previously subcloned from a pulmonary KS tumor as 10–15 kb overlapping segments in l phage (Gao, et al., 1994). DNA was prepared from a clone known to encode the thymidine kinase (TK) gene from which a 5.8 kb BamHI-HindIII DNA fragment was subcloned into Bluescript II KS (Stratagene, LaJolla, Calif.), according to methods known in the art. A HindIII, SacI digest resulted in four KS-specific DNA fragments of 1.9 kb, 1.5 kb, 1.1 kb and 0.8 kb. These fragments were subcloned into Bluescript and sequenced using T3 and T7 primers. The 1.5 kb and 0.8 kb fragments contained DNA sequences that encoded a protein that aligned with herpesvirus saimiri (HVS) Pr sequences. The nucleotide sequence of these fragments was determined by sequencing both strands of the DNA. Synthetic oligonucleotide primers were used to generate overlapping sequences of the entire insert. The primers were synthesized on an Applied Biosystems 391 DNA synthesizer. Automated DNA sequencing was carried out using an Applied Biosystems 377 Prism sequencer, and manual DNA sequencing was carried out using standard conditions.

EXAMPLE 2

Bacterial Expression of KSHV Protease
1. Construction of Expression Vectors

A linear DNA fragment containing the KSHV Pr domain was amplified from the plasmid pBS1.5 (see FIG. 1) using the polymerase chain reaction (PCR). The 5' primer for this amplification was 5'-GG GGG TCC GGA CAG GGC CTG TAC GTC GGA-3' (SEQ ID NO:16), and the 3' primer 5'-GG GGG AAG CTT CTA GGC CTT TAA ATA CAC CGG-3' (SEQ ID NO:17).

In order to create a bacterial expression vector for KSHV Pr, the product of the PCR reaction was digested with the restriction endonucleases BamHI and HindIII prior to ligation into similarly treated pQE30 DNA (Qiagen, Chatsworth, Calif.). This construct (pHis$_6$-KSP), designed to over-express the wild-type Pr with the amino acid sequence Met-Arg-Gly-Ser-His$_6$-Gly-Ser replacing the initiating Met residue (His$_6$-Pr), allows for affinity purification of the His-tagged enzyme through the use of metal chelate chromatography. This plasmid was propagated in the E. coli strain XL1-Blue (Stratagene, LaJolla, Calif.) to alleviate DNA degradation and rearrangement.

The substitution of Ser114, encoded by TCT, to Ala (GCC) was performed by PCR-mediated site-directed mutagenesis of the Pr ORF (Ausubel, et al., 1990). The DNA oligonucleotides 5'-CTC CCG GGG CTG GCC TTA TCG TCC ATA C-3' (SEQ ID NO:18) and 5'-TAT GGA CGA TAA GGC CAG CCC CGG GAG-3' (SEQ ID NO:19), corresponding to the mutated upper and lower strands, respectively, were used to introduce the substitutions into the Pr ORF (the mismatched bases are underlined). These PCR products were gel-purified and subjected to a second round of PCR in order to construct the full-length coding sequence of His$_6$-Pr(S114A). The presence of the correct substitution was verified by DNA sequence analysis, subsequent to insertion into the BamHI and HindIII restriction sites of pQE30 to construct the plasmid pHis$_6$-KSP(S114A).

A. Bacterial Growth and Protein Expression

The above-described plasmids were separately transformed into the E. coli strain X-90 to afford high-level expression of recombinant protease gene products (Evnin, et al., 1990). Bacterial cultures were grown at 37° C. in LB medium to an OD$_{600}$=0.8, and isopropyl β-D-thiogalactopyranoside (IPTG) was added to a concentration of 0.2 mM. Cultures were then grown for 3 hours to allow for protein expression, and harvested by centrifugation. Purification was as described in Example 3.

Alternatively, the protein can be expressed in the periplasmic space of bacteria using the expression vector pTac Ecotin. Here, JM101 cells are freshly transformed with expression plasmid DNA encoding the KSHV protease or the KSHV protease-assembly protein precursor. A single colony selected from ampicillin plates is used to inoculate LB/ampicillin liquid culture. The cultures are grown and expression induced with IPTG. The cells are harvested and lysed with lysozyme in a sucrose solution to prevent lysis of the inner cell membrane. The spheroplasts are pelleted and the periplasmic fraction collected and dialyzed against sodium citrate (pH 2.8). The supernatant is adjusted to pH 7.4 and 0.3 M NaCl, and the solution is heated in boiling water for 10 minutes, then is cooled to room temperature. The resulting precipitate is removed by centrifugation and the remaining supernatant is dialyzed against water and purified by C4-reverse-phase HPLC chromatography. This method produces as much as 10 milligrams of pure crystallizable protein per liter of culture.

B. Expression in Yeast

A Saccharomyces cerevisiae system with a hybrid ADH-GAPDH promoter is used. Protein is secreted into the media through the use of an alpha-factor leader sequence (Russo, et al., 1996). A second system involves the use of the methylotropic yeast P. pastoris (Invitrogen, San Diego, Calif.). The cloning vectors for this system contain alcohol oxidase 1 (AOX1) promoter and termination sequences, in addition to the His4 gene. The linearized vectors are introduced into yeast by electroporation and colonies are screened as directed by the Invitrogen instructions. Induction of protein expression occurs upon addition of methanol, and secretion into the media is directed by the alpha-factor leader sequence or the acid phosphatase leader sequence (Schalling, et al., 1995).

C. Baculovirus Expression

Insect cells and the lytic baculovirus Autographa californica nuclear polyhidrosis virus (AcNPV) are used. Transfer vector constructs are made, utilizing gp67 secretion signal sequence, and the strong baculovirus polyhedron promoter. Cotransfection with the linearized baculovirus genome (BaculoGold™ DNA; PharMingen, (San Diego, Calif.) normally yields a high level of recombinant viruses. A single recombinant baculovirus is obtained by plaque purification and subsequently amplified and used for protein expression.

EXAMPLE 3

Purification of KSHV Protease

Bacterial cell pellets, as obtained as described in Example 2, were resuspended in sonication buffer (50 mM Tris-HCl (pH 8.0), 0.5 M KCl, 10% (v/v) glycerol, 1 mM β-mercaptoethanol), and sonicated on ice. Lysates were then pelleted at 10,000×g, and the insoluble matter resuspended in denaturing buffer (50 mM Tris-HCl (pH 8.0), 100 mM NaCl, 1 mM b-mercaptoethanol), containing 6 M deionized urea, by slowly stirring on ice for 30 minutes. The resuspended pellet was then centrifuged as above, and the supernatant was incubated with 3 to 4 ml Ni-NTA agarose (Qiagen, Chatsworth, Calif.), which had been equilibrated in denaturing buffer/urea, by slow stirring on ice for 1 hour. This slurry was packed into a column reservoir, and subjected to a 1 L reverse urea gradient, from 6 M to 0 M urea, in denaturing buffer. The refolded, Ni-bound proteins were then washed in column buffer (50 mM Tris-HCl (pH 8.0), 500 mM KCl, 1 mM b-mercaptoethanol, 10% glycerol) containing 0.01% (v/v) Tween-20 and 10 mM imidazole, before equilibrating the column in the absence of Tween-20. Bound protein was then eluted using a 10 mM–0.5 M imidazole gradient in column buffer. Protein-containing fractions were pooled and dialyzed against storage buffer (50 mM Tris-HCl (pH 8.0), 100 mM KCl, 10% glycerol, 0.1 mM DTT) before aliquoting and freezing at −80° C. Protein concentrations were estimated using a calculated e280 of 0.9 ml mg$^{-1}$ cm$^{-1}$.

EXAMPLE 4

Antibody Production and Immunoblot Analysis

Polyclonal antiserum was raised in rabbits against purified KSHV His$_6$-Pr (Animal Pharm Services, Inc., Healdsburg, Calif.). For immunoblot analysis, protein samples were run on a 10% polyacrylamide-SDS gel and transferred to a nitrocellulose membrane (Schleicher & Schuell, Keene, N.H.). The membrane was treated with Tris-buffered saline with 0.1% (v/v) Triton X-100 (TBST) containing 5% (w/v) nonfat dry milk, washed with TBST containing 1% milk, and probed with a 1:250 dilution of the anti-protease (α-KSP) polyclonal serum in the same buffer. After washing as above, a 1:5000 dilution of goat anti-rabbit horseradish peroxidase-conjugated serum (Pierce, Rockford Ill.) was then applied in TBST/1% milk. Antibody-bound protein bands were detected by enhanced chemiluminescence (Amersham, Arlington Heights, Ill.).

EXAMPLE 5

Fluorometric Enzyme Assay

Protease assays using the fluorogenic peptide substrate DABCYL-Arg-Gly-Val-Val-Asn-Ala-Ser-Ser-Arg-Leu-Ala-EDANS, where RGVVNASSRLA (SEQ ID NO:15) was obtained from BACHEM (King of Prussia, Pa.), were monitored optically by a Perkin-Elmer LS-5B luminescence spectrophotometer interfaced with a Macintosh SE-30 computer. DABCYL represents 4-(4'-Dimethylaminophenylazo) benzoic acid, and EDANS signifies (2'-aminoethylamino)-naphthalene-1-sulfonic acid. His$_6$-Pr and His$_6$-Pr(S114A) were diluted 10-fold from storage buffer into assay buffer (50 mM NaOAc (pH 5.5), 20% (v/v) glycerol, 0.1 mM EDTA, 0.1 mM DTT), equilibrated to 37° C. for 5 minutes in thermostatted quartz cuvettes, and manually mixed with a final substrate concentration of 10 µM. A pH 5.5 buffer was utilized due to slightly higher proteolytic activity than that observed in pH 7.5 Tris-based solutions. The final KSHV Pr concentrations were 1.5 µM. Time-evolved fluorescence enhancement was followed by exciting the samples at 355 nm and detecting emission at 495 nm. Trypsin and its D102N variant (Craik, et al., 1987) were diluted into the same assay buffer to final concentrations of 1 nM and 1 µM, respectively, and treated identically to the KSHV enzymes. The ratio of fluorescence at each time point (F) was then compared with the initial fluorescence output (F$_O$) to generate plots of F/F$_O$ vs. time.

The above assay can also be carried out using KSHV derived peptides, such as the KSHV R-site and M-site peptides described herein.

The inhibitory activity of Boc-YLKA-COCH$_2$Cl was assayed against the autolytically stable Pr(S204G) variant using essentially the same procedure as described above. The enzyme and inhibitor (0.5 μM and 300 μM, respectively) were pre-incubated for 15 minutes prior to initiating the assay by addition of 20 μM of the fluorogenic substrate.

EXAMPLE 6

Northern Blot Analysis

BCBL-1 cells (Renne, et al., 1996) were treated with phosphoroformic acid (PFA) at a concentration of 500 mM for at least 3 days prior to induction. Untreated and PFA treated cells were then split into identical flasks, at 3×10$^5$ cells/ml, and left unstimulated or induced with 12-O-tetradecanoyl phorbol-13-acetate (TPA) at a concentration of 20 ng/ml. After 48 hours, total RNA was harvested using RNAzol B as recommended by the manufacturer (Tel-Test, Friendwood, Tex.). To enrich the polyadenylated RNA fraction, 300 μg RNA samples, uninduced and induced with TPA, and with and without PFA treatment, were affinity purified using the Oligotex mRNA purification system (Qiagen, Chatsworth, Calif.). RNA was separated on a 1% agarose, 17% formaldehyde gel, transferred to Hybond-N nylon membrane in 10× SSC for 5 hours, and UV-crosslinked. The 1.5 kb insert from pBS1.5 was gel purified and labelled using the rediPrime Random Prime kit (Amersham Corporation, Arlington Heights, Ill.). Hybridization was performed as according to standard methods (Renne, et al., 1996), and the blot was exposed to Kodak XAR5 film for 8 hours.

While the invention has been described with reference to specific methods and embodiments, it will be appreciated that various modifications and changes may be made without departing from the invention.

It is claimed:

1. An expression vector for recombinant expression of a KSHV protease, comprising
   a polynucleotide encoding a KSHV protease having (i) a release site identified by SEQ ID NO:12 and (ii) proteolytic activity, as evidenced by cleavage of a synthetic peptide substrate containing the peptide sequence identified by SEQ ID NO:15, said expression vector including regulatory elements effective for expression of the protease encoded by the polynucleotide in a suitable host.

2. The expression vector of claim 1 wherein the polynucleotide has the sequence identified as SEQ ID NO:6.

3. The expression vector of claim 1, wherein the KSHV protease encoded by said polynucleotide has the sequence identified by SEQ ID NO:7.

4. A host cell containing the expression vector of claim 1.

5. A method for recombinant production of a KSHV protease, comprising the steps of (a) culturing the host cell of claim 4 under conditions suitable for expression of the protease, and (b) recovering the protease from the host cell or cell culture medium.

6. The expression vector of claim 1, wherein the KSHV protease encoded by said polynucleotide has the sequence set forth as SEQ ID NO:7 with an amino acid other than Ser at position 204.

7. The expression vector of claim 1, wherein the KSHV protease encoded by said polynucleotide has the sequence set forth as SEQ ID NO:7 with a Gly in place of Ser at position 204.

8. An expression vector for recombinant expression of a KSHV polypeptide, comprising
   a polynucleotide encoding a KSHV protease/assembly protein having (i) a release site identified by SEQ ID NO:12, (ii) a maturation site identified by SEQ ID NO:13 and (iii) proteolytic activity, as evidenced by cleavage of a synthetic peptide substrate containing the peptide sequence identified by SEQ ID NO:15, said expression vector including regulatory elements effective for expression of the polypeptide encoded by the polynucleotide in a suitable host.

9. The expression vector of claim 8, wherein the polynucleotide has a sequence selected from the group consisting of SEQ ID NO:1, SEQ ID NO:4 and SEQ ID NO:5.

10. An expression vector for recombinant expression of a KSHV protease, comprising
    a polynucleotide encoding a KSHV protease having (i) a release site identified by SEQ ID NO:12 and (ii) proteolytic activity on a maturation site identified by SEQ ID NO:13, said expression vector including regulatory elements effective for expression of the protease encoded by the polynucleotide in a suitable host.

11. The expression vector of claim 10 wherein the polynucleotide has the sequence identified as SEQ ID NO:6.

12. A host cell containing the expression vector of claim 10.

13. The expression vector of claim 10, wherein the KSHV protease encoded by said polynucleotide has the sequence SEQ ID NO:7.

* * * * *